(12) United States Patent
Bergeron, Jr.

(10) Patent No.: US 9,125,950 B2
(45) Date of Patent: Sep. 8, 2015

(54) SIDEROPHORE CONJUGATE IMMUNOGENIC COMPOSITIONS AND VACCINES

(71) Applicant: University of Florida Research Foundation, Inc., Gainesville, FL (US)

(72) Inventor: Raymond J. Bergeron, Jr., Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/486,504

(22) Filed: Sep. 15, 2014

(65) Prior Publication Data

US 2015/0071961 A1    Mar. 12, 2015

Related U.S. Application Data

(62) Division of application No. 13/265,651, filed as application No. PCT/US2010/031675 on Apr. 20, 2010, now Pat. No. 8,834,890.

(60) Provisional application No. 61/171,151, filed on Apr. 21, 2009.

(51) Int. Cl.

| A61K 39/385 | (2006.01) |
| A61K 47/48 | (2006.01) |
| A61K 39/02 | (2006.01) |
| C07K 16/12 | (2006.01) |
| A61K 39/00 | (2006.01) |

(52) U.S. Cl.
CPC ......... *A61K 47/48276* (2013.01); *A61K 39/107* (2013.01); *A61K 39/385* (2013.01); *A61K 47/4833* (2013.01); *A61K 47/48284* (2013.01); *C07K 16/1239* (2013.01); *A61K 2039/6031* (2013.01); *A61K 2039/6068* (2013.01); *A61K 2039/6081* (2013.01)

(58) Field of Classification Search
None
See application file for complete search history.

(56) References Cited

U.S. PATENT DOCUMENTS

| 7,413,743 | B2 | 8/2008 | Emery et al. |
| 8,834,890 | B2 | 9/2014 | Bergeron, Jr. |
| 2002/0058326 | A1 | 5/2002 | O'Sullivan |
| 2004/0191233 | A1 | 9/2004 | O'Sullivan |
| 2006/0019279 | A1 | 1/2006 | Bosse et al. |
| 2006/0079580 | A1 | 4/2006 | Moore et al. |
| 2008/0193373 | A1 | 8/2008 | Stritzker et al. |

FOREIGN PATENT DOCUMENTS

| EP | 0 389 347 A1 | 9/1990 |
| WO | WO 2008/115959 A1 | 9/2008 |
| WO | WO 2010/033847 A1 | 3/2010 |

OTHER PUBLICATIONS

Ellis, R.W. (Chapter 29 of "Vaccines" [Plotkin, S.A. et al. (eds) published by W. B. Saunders company (Philadelphia), 568-575, 1988.*
Extended European Search Report for EP 10767606.6, mailed Jan. 8, 2014.
International Search Report and Written Opinion for PCT/US2010/031675, mailed Dec. 30, 2010.
International Preliminary Report on Patentability for PCT/US2010/031675, mailed Nov. 3, 2011.
[No Author Listed], "Antigenic Determinant". Illustrated Dictionary of Immunology. 2$^{th}$ edition. Cruse et al., ed. 2003;46.
Abaza et al., Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.
Al Moudallal et al., Monoclonal antibodies as probes of the antigenic structure of tobacco mosaic virus. EMBO J. 1982;1(8):1005-10.
Bergeron et al., A comparative evaluation of iron clearance models. Ann N Y Acad Sci. 1990;612:378-93.
Bergeron et al., A comparative study of the iron-clearing properties of desferrithiocin analogues with desferrioxamine B in a Cebus monkey model. Blood. Apr. 15, 1993;81(8):2166-73.
Bergeron et al., An efficient total synthesis of agrobactin and its gallium(III) chelate. J Org Chem. 1985;50:2780-82.
Bergeron et al., An efficient total synthesis of desferrioxamine B. J Org Chem. 1988;53:3131-34.
Bergeron et al., Effects of C-4 stereochemistry and C-4" hydroxylation on the iron clearing efficiency and toxicity of desferrithiocin analogues. J Med Chem. Jul. 1, 1999;42(13):2432-40.
Bergeron et al., Short synthesis of parabactin. J Am Chem Soc. 1982;104:4489-92.
Bergeron et al., Synthesis of N4-acylated N1,N8-bis(acyl)spermidines. An approach to the synthesis of siderophores. J Org Chem. 1980;45:1589-92.
Bergeron et al., Synthesis of reagents for the construction of hypusine and deoxyhypusine peptides and their application as peptidic antigens. J Med Chem. Sep. 24, 1998;41(20):3888-900.
Bergeron et al., The total synthesis of alcaligin. J Org Chem. 1991;56:5560-63.
Bergeron et al., The total synthesis of bisucaberin. Tetrahedron. 1989;45:4939-44.
Bergeron et al., The total synthesis of desferrioxamines E and G. Tetrahedron. 1990;46:5881-88.
Bergeron et al., The total synthesis of nannochelin: a novel cinnamoyl hydroxamate-containing siderophore. J Org Chem. 1992;57:7140-43.
Bergeron et al., Total synthesis of vibriobactin. Tetrahedron. 1985;41:507-10.
Bergeron et al., Vibriobactin antibodies: a vaccine strategy. J Med Chem. Jun. 25, 2009;52(12):3801-13. doi: 10.1021/jm900119q.
Bergeron, Iron: A Controlling Nutrient in Proliferative Processes. Trends in Biochem Sci. 1986;11:133-36.

(Continued)

*Primary Examiner* — Brian J Gangle
(74) *Attorney, Agent, or Firm* — Wolf, Greenfield & Sacks, P.C.

(57) ABSTRACT

An immunogenic composition comprising a siderophore covalently linked to a pharmaceutically acceptable carrier molecule wherein the antigenicity of the siderophore moiety is sufficient to stimulate an immunologic response to the siderophore when the composition is circulating in the bloodstream of a human or non-human animal and vaccine.

10 Claims, 9 Drawing Sheets

(56) References Cited

OTHER PUBLICATIONS

Bergeron, Synthesis and solution structure of microbial siderophores. Chem Rev. 1984;84:587-602.

Bernier et al., Desketoneoenactin-siderophore conjugates for *Candida*: evidence of iron transport-dependent species selectivity. Antimicrob Agents Chemother. Jan. 2005;49(1):241-8.

Butterton et al., Cloning, sequencing, and transcriptional regulation of viuA, the gene encoding the ferric vibriobactin receptor of *Vibrio cholerae*. J Bacteriol. Jun. 1992;174(11):3729-38.

Byers et al., Microbial iron transport: iron acquisition by pathogenic microorganisms. Met Ions Biol Syst. 1998;35:37-66.

Chipperfield et al., Salicylic acid is not a bacterial siderophore: a theoretical study. Biometals. Jun. 2003;13(2):165-8.

Crosa, Signal transduction and transcriptional and post-transcriptional control of iron-regulated genes in bacteria. Microbiol Mol Biol Rev. Sep. 1997;61(3):319-36.

Ellis, New Technologies for Making Vaccines. Vaccines. Plotkin et al., ed. 1988;568-75.

Esteve-Gassent et al., Immunogenic antigens of the eel pathogen *Vibrio vulnificus* serovar E. Fish Shellfish Immunol. Sep. 2004;17(3):277-91.

Fletcher et al., Mild, efficient and rapid O-debenzylation of ortho-substituted phenols with trifluoroacetic acid. Tetrahedron Lett. 2008;49:4817-19.

Griffiths et al., Vibriobactin, a siderophore from *Vibrio cholerae*. J Biol Chem. Jan. 10, 1984;259(1):383-5.

Henderson et al., *Vibrio cholerae* iron transport systems: roles of heme and siderophore iron transport in virulence and identification of a gene associated with multiple iron transport systems. Infect Immun. Nov. 1994;62(11):5120-5.

Janoki et al., [67Ga]desferrioxamine—HSA: synthesis of chelon protein conjugates using carbodiimide as a coupling agent. Int J Appl Radiat Isot. Jun. 1983;34(6):871-7.

Kalinowski et al., The evolution of iron chelators for the treatment of iron overload disease and cancer. Pharmacol Rev. Dec. 2005;57(4):547-83.

Kao et al., A monoclonal antibody-based enzyme-linked immunosorbent assay for quantitation of plasma thrombospondin. Am J Clin Pathol. Sep. 1986;86(3):317-23.

Kim et al., A widespread deferoxamine-mediated iron-uptake system in *Vibrio vulnificus*. J Infect Dis. Nov. 15, 2007;196(10):1537-45. Epub Oct. 31, 2007.

Le Roy et al., Activity and specificity of a mouse monoclonal antibody to ferric aerobactin. Infect Immun. Mar. 1992;60(3):768-72.

Litwin et al., Role of catechol siderophore synthesis in *Vibrio vulnificus* virulence. Infect Immun. Jul. 1996;64(7):2834-8.

Litwin et al., Role of iron in regulation of virulence genes. Clin Microbiol Rev. Apr. 1993;6(2):137-49.

McGuinness et al., Class 1 outer membrane protein of *Neisseria meningitidis*: epitope analysis of the antigenic diversity between strains, implications for subtype definition and molecular epidemiology. Mol Microbiol. Feb. 1993;7(4):505-14.

Miller et al., Siderophore-Mediated Drug Delivery: The Design, Synthesis, and Study of Siderophore-Antibiotic and Antifungal Conjugates. In: The Devolpment of Iron Chelators for Clinical Use. Bergeron et al., eds. CRC: Boca Raton. 1994:275-06.

Neilands, Siderophores: structure and function of microbial iron transport compounds. J Biol Chem. Nov. 10, 1995;270(45):26723-6.

Nicholson et al., Disruption of tonB in *Bordetella bronchiseptica* and *Bordetella pertussis* prevents utilization of ferric siderophores, haemin and haemoglobin as iron sources. Microbiology. Sep. 1999;145 ( Pt 9):2453-61.

Occhino et al., *Vibrio cholerae* iron transport: haem transport genes are linked to one of two sets of tonB, exbB, exbD genes. Mol Microbiol. Sep. 1998;29(6):1493-507.

Ochsner et al., Genetics and regulation of two distinct haem-uptake systems, phu and has, in *Pseudomonas aeruginosa*. Microbiology. Jan. 2000;146 ( Pt 1):185-98.

Okujo et al., Involvement of vulnibactin and exocellular protease in utilization of transferrin- and lactoferrin-bound iron by *Vibrio vulnificus*. Microbiol Immunol. 1996;40(8):595-8.

Payne et al., Siderophore production by *Vibrio cholerae*. Infect Immun. Apr. 1978;20(1):310-1.

Ponka et al., Function and regulation of transferrin and ferritin. Semin Hematol. Jan. 1998;35(1):35-54.

Ratledge et al., Iron metabolism in pathogenic bacteria. Annu Rev Microbiol. 2000;54:881-941.

Simpson et al., Siderophore production by *Vibrio vulnificus*. Infect Immun. Aug. 1983;41(2):644-9.

Simrell et al., Antibody responses of tumor-bearing mice to their own tumors captured and perpetuated as hybridomas. J Immunol. Nov. 1979;123(5):2386-94.

Stelma et al., Virulence characteristics of clinical and environmental isolates of *Vibrio vulnificus*. Appl Environ Microbiol. Sep. 1992;58(9):2776-82.

Stoebner et al., Identification of the vibriobactin receptor of *Vibrio cholerae*. J Bacteriol. May 1992;174(10):3270-4.

Stoebner et al., Iron-regulated hemolysin production and utilization of heme and hemoglobin by *Vibrio cholerae*. Infect Immun. Nov. 1988;56(11):2891-5.

Stojiljkovic et al., *Neisseria meningitidis* tonB, exbB, and exbD genes: Ton-dependent utilization of protein-bound iron in *Neisseriae* . . . J Bateriol. 1997;179:805-812.

Theil et al., Ferritin Mineralization: Ferroxidation and Beyond. J Inorg Biochem. 1997;67:30. Abstract B13.

Walz et al., Synthesis and studies of catechol-containing mycobactin S and T analogs. Org Biomol Chem. May 21, 2007;5(10):1621-8. Epub Apr. 19, 2007.

Webster et al., Cloning and characterization of vuuA, a gene encoding the *Vibrio vulnificus* ferric vulnibactin receptor. Infect Immun. Feb. 2000;68(2):526-34.

Yuan et al., Characterization of the *Ustilago maydis* sid2 gene, encoding a multidomain peptide synthetase in the ferrichrome biosynthetic gene cluster. J Bacteriol. Jul. 2001;183(13):4040-51.

\* cited by examiner 1 desferrioxamine B (DFO)

2  R = H   vulnibactin
3  R = OH  vibriobactin (VIB)

Naturally occurring iron chelators (siderophores):hydroxamates (1) and catecholamides (2 and 3).

4  R = OVA (OVA-VIB)
5  R = BSA (BSA-VIB)

6

36

SIDEROPHORE CONJUGATE IMMUNOGENIC COMPOSITIONS AND VACCINES

PRIORITY DATA

This application claims the benefit of U.S. Provisional Application No. 61/171,151 filed Apr. 21, 2009, said application hereby incorporated by reference in its entirety.

U.S. GOVERNMENT GRANT

Research leading to the inventions described herein was conducted under a grant from NIH: 5R37DK049108.

BACKGROUND OF THE INVENTION

Iron occurs in oxidation states from −2 to +6 depending on both pH and the nature of the ligating groups surrounding the metal [Bergeron, R. J.; Brittenham, G. M. *The Development of Iron Chelators for Clinical Use*. CRC: Boca Raton, Fla., 1994]. It is these dependencies that nature has exploited so effectively in enlisting the metal as a central component in a myriad of redox processes [Bergeron, R. J.; McManis, J. S.; Wiegand, J.; Weimar, W. R. A Search for Clinically Effective Iron Chelators. In *Iron Chelators: New Development Strategies*, Badman, D. G.; Bergeron, R. J.; Brittenham, G. M., Eds. Saratoga: Ponte Vedra Beach, Fla., 2000; pp 253-292]. In fact, life without iron is virtually nonexistent [Crichton, R. R. *Inorganic Biochemistry of Iron Metabolism*. J. Wiley & Sons: Chichester, UK, 2001]. However, while the metal composes some 5% of the earth's crust, it is nevertheless difficult for living systems to access. In the biosphere, iron exists largely as Fe (III), in a variety of water insoluble forms, at pH 7. The concentration of free Fe(III) under these conditions is ≈1.4× $10^{-9}$ M [Chipperfield, J. R.; Ratledge, C. Salicylate Is Not a Bacterial Siderophore: A Theoretical Study. *BioMetals* 2000, 13, 165-168], somewhat lower than that required to support most life forms. In the presence of phosphate ions in culture media and potential animal hosts, the free Fe(III) concentration in solution drops even further, by a factor of 10.

Both prokaryotes and eukaryotes have overcome the problem of iron accessibility by developing iron-binding ligands and associated transport systems [Bernier, G.; Girijavallabhan, V.; Murray, A.; Niyaz, N.; Ding, P.; Miller, M. J.; Malouin, F. Desketoneoenactin-Siderophore Conjugates for Candida: Evidence of Iron Transport-Dependent Species Selectivity. *Antimicrob. Agents Chemother.* 2005, 49, 241-248; Walz, A. J.; Mollmann, U.; Miller, M. J. Synthesis and Studies of Catechol-Containing Mycobactin S and T Analogs. *Org. Biomol. Chem.* 2007, 5, 1621-1628; Yuan, W. M.; Gentil, G. D.; Budde, A. D.; Leong, S. A. Characterization of the Ustilago maydis sid2 Gene, Encoding a Multidomain Peptide Synthetase in the Ferrichrome Biosynthetic Gene Cluster. *J. Bacteriol.* 2001, 183, 4040-4051; Byers, B. R.; Arceneaux, J. E. Microbial Iron Transport: Iron Acquisition by Pathogenic Microorganisms. *Met. Ions Biol. Syst.* 1998, 35, 37-66; Kalinowski, D. S.; Richardson, D. R. The Evolution of Iron Chelators for the Treatment of Iron Overload Disease and Cancer. *Pharmacol Rev.* 2005, 57, 547-583; Bergeron, R. J. Iron: A Controlling Nutrient in Proliferative Processes. *Trends Biochem. Sci.* 1986, 11, 133-136; Theil, E. C.; Huynh, B. H. Ferritin Mineralization: Ferroxidation and Beyond. *J. Inorg. Biochem.* 1997, 67, 30 and Ponka, P.; Beaumont, C.; Richardson, D. R. Function and Regulation of Transferrin and Ferritin. *Semin. Hematol.* 1998, 35, 35-54]. Prokaryotes produce a group of iron chelators or siderophores (generally low-molecular weight, iron-specific ligands) that they secrete into the environment. These ligands often present with very large formation constants (e.g., $10^{48}$ $M^{-1}$) [Bergeron, R. J.; McManis, J. S. Synthesis of Catecholamide and Hydroxamate Siderophores. In *CRC Handbook of Microbial Iron Chelates*, Winkelmann, G., Ed. CRC: Boca Raton, 1991; pp 271-307] and can effectively remove the metal from other donor arrays. The resulting metal complex, a ferrisiderophore, is then taken up by microorganisms [Ratledge, C.; Dover, L. G. Iron Metabolism in Pathogenic Bacteria. *Annu. Rev. Microbiol.* 2000, 54, 881-941; Nicholson, M. L.; Beall, B. Disruption of tonB in *Bordetella bronchiseptica* and *Bordetella pertussis* Prevents Utilization of Ferric Siderophores, Haemin, and Haemoglobin as Iron Sources. *Microbiology* 1999, 145, 2453-2461 and Occhino, D. A.; Wyckoff, E. E.; Hernderson, D. P.; Wrona, T. J.; Payne, S. M. *Vibrio cholerae* Iron Transport: Haem Transport Genes Are Linked to One of Two Sets of tonB, exbB, exbD Genes. *Mol. Microbiol.* 1998, 29, 1493-1507], most often beginning with binding to an outer membrane receptor [Stojiljkovic, I.; Srinivasan, N. *Neisseria meningitidis* tonB, exbB, and exbD Genes: Ton-Dependent Utilization of Protein-Bound Iron in Neisseriae. *J. Bacteriol.* 1997, 179, 805-812]. This is followed by shuttling the iron complex through the periplasm and finally, to the cytoplasm, where the iron is freed up. These ferrisiderophore transporters are energy-dependent, often exploiting the tonB system [Griffiths, E.; Williams, P. H. *The Iron-Uptake Systems of Pathogenic Bacteria, Fungi, and Protozoa*. 2 ed.; John Wiley & Sons: Chichester, UK, 1999; Ochsner, U. A.; Johnson, Z.; Vasil, M. L. Genetics and Regulation of Two Distinct Haem-Uptake Systems, phu and has, in *Pseudomonas aeruginosa*. *Microbiology* 2000, 146, 185-198 and Stoebner, J. A.; Payne, S. M. Iron-Regulated Hemolysin Production and Utilization of Heme and Hemoglobin by *Vibrio cholerae*. *Infect. Immun.* 1988, 56, 2891-2895]. In most instances, the desferrisiderophore is released to further gather iron.

There have now been over 500 different siderophores identified [Drechsel, H.; Winkelmann, G. Iron Chelation and Siderophores. In *Transition Metals in Microbial Metabolism*, Winkelmann, G., Carrano, C. J., Eds. Harwood Acad.: Amsterdam, the Netherlands, 1997; pp 1-9.; Neilands, J. B. Siderophores: Structure and Function of Microbial Iron Transport Compounds. *J. Biol. Chem.* 1995, 270, 26723-26726; Telford, J. R.; Raymond, K. N. Siderophores. In *Comprehensive Supramolecular Chemistry*, Atwood, J. L., Davies, J. E. D., MacNicol, D. D., Vogtle, F., Lehn, J.-M., Eds. Elsevier Sci.: Oxford, UK, 1996; Vol. 1, pp 245-266; Winkelmann, G. *CRC Handbook of Microbial Iron Chelates*. CRC: Boca Raton, Fla., 1991 and Winkelmann, G.; Drechsel, H. *Microbial Siderophores. Biotechnology*. 2 ed.; Verlag Chem.: Weinheim, Germany, 1997; Vol. 7]. While there are certainly exceptions, the two main classes of natural product iron chelators are hydroxamates [Bergeron, R. J.; Phanstiel, O., IV. The Total Synthesis of Nannochelin: A Novel Cinnamoyl Hydroxamate-Containing Siderophore. *J. Org. Chem.* 1992, 57, 7140-7143; Bergeron, R. J.; McManis, J. S. Synthesis and Biological Activity of Hydroxamate-Based Iron Chelators. In *The Development of Iron Chelators for Clinical Use*, Bergeron, R. J.; Brittenham, G. M., Eds. CRC: Boca Raton, 1994; pp 237-273; Bergeron, R. J.; McGovern, K. A.; Channing, M. A.; Burton, P. S. Synthesis of $N^4$-Acylated $N^1$,$N^8$-Bis(Acyl) Spermidines: An Approach to the Synthesis of Siderophores. *J. Org. Chem.* 1980, 45, 1589-1592; Bergeron, R. J.; Kline, S. J. Short Synthesis of Parabactin. *J. Am. Chem. Soc.* 1982, 104, 4489-4492; Bergeron, R. J.; McManis, J. S.; Dionis, J. B.; Garlich, J. R. An Efficient Total Synthesis of Agrobactin and Its Gallium(III) Chelate. *J. Org. Chem.* 1985, 50, 2780-2782 and Bergeron, R. J.; Garlich, J. R.; McManis, J. S. Total Synthesis of Vibriobactin. *Tetrahedron* 1985, 41, 507-510], such as desferrioxamine (1) and catecholamides [Bergeron, R. J.; Pegram, J. J. An Efficient Total Synthesis of Desferrioxamine. *J. Org. Chem.* 1988, 53, 3131-3134; Bergeron, R. J.; McManis, J. S. The Total Synthesis of Desferrioxamines E and G. *Tetrahedron* 1990, 46, 5881-5888; Bergeron, R. J. Synthesis and Solution Structures of Microbial Siderophores. *Chem. Rev.* 1984, 84, 587-602; Bergeron, R. J.; McManis, J. S. Total Synthesis of Bisucaberin. *Tetrahedron* 1989, 45, 4939-4944 and Bergeron, R. J.; McManis, J. S.; Perumal, P. T.; Algee, S. E. The Total Synthesis of Alcaligin. *J. Org. Chem.* 1991, 56, 5560-5563], including vulnibactin (2) and vibriobactin (3) (FIG. 1). Some microorganisms can, in fact, utilize more than one type and/or class of siderophores [Kim, C.-M.; Park, Y.-J.; Shin, S.-H. A Widespread Desferrioxamine-Mediated Iron-Uptake System in *Vibrio vulnificus*. *J. Infect. Dis.* 2007, 196, 1537-1545].

Iron acquisition becomes somewhat more problematic for microorganisms in an in vivo situation (e.g., in humans). Pathogens have additional iron acquisition hurdles to overcome beyond low metal solubility. Animals, for example, have an iron-withholding system: proteinaceous iron chelators that make iron acquisition difficult for microorganisms. There is little of the free metal available in animals. It is generally bound to heme (iron-containing enzymes) by transferrin, (an iron shuttle protein) or stored in ferritin. In each instance, iron is not easily accessible to microorganisms.

The opportunistic microorganism *Vibrio vulnificans* nicely illustrates how pathogens can overcome host iron-withholding [Stoebner, J. A.; Butterton, J. R.; Calderwood, S. B.; Payne, S. M. Identification of the Vibriobactin Receptor of *Vibrio cholerae*. *J. Bacteriol.* 1992, 174, 3270-3274]. The siderophore produced by *Vibrio vulnificans*, vulnibactin (2) (FIG. 1), cannot remove iron from transferrin, the ever-present iron shuttle protein in plasma, in spite of the fact 2 binds iron more tightly than transferrin. The chelator cannot access transferrin iron, as it is bound within the protein.

To solve this problem, the microorganism secretes a protease, which cleaves transferrin, thus releasing iron. The metal is then sequestered by 2, and the ferrisiderophore is taken up via an intermembrane receptor, viuA [Butterton, J. R.; Stoebner, J. A.; Payne, S. M.; Calderwood, S. B. Cloning, Sequencing, and Transcriptional Regulation of vuuA, the Gene Encoding the Ferric Vibriobactin Receptor of *Vibrio cholerae*. *J. Bacteriol.* 1992, 174, 3729-3738; Simpson, L. M.; Oliver, J. D. Siderophore Production by *Vibrio vulnificus*. *Infect. Immun.* 1983, 41, 644-649 and Okujo, N.; Akiyama, T.; Miyoshi, S.; Shinoda, S.; Yamamoto, S. Involvement of Vulnibactin and Exocellular Protease in Utilization of Transferrin- and Lactoferrin-Bound Iron by *Vibrio vulnificus*. *Microbiol. Immunol.* 1996, 40, 595-598].

In fact, *Vibrio vulnificans* mutants without the vulnibactin transporter have reduced pathogenicity in mice [Webster, A. C. D.; Litwin, C. M. Cloning and Characterization of vuuA, a Gene Encoding the *Vibrio vulnificus* Ferric Vulnibactin Receptor. *Infect. Immun.* 2000, 68, 526-534]. This uptake apparatus has been shown to have significant homology with the *Vibrio cholerae* receptor. However, while it seems clear from studies with genetically altered microorganisms that shutting down the siderophore iron-uptake system can slow growth and reduce pathogenicity, microorganisms can still access iron via other mechanisms [Henderson, D. P.; Payne, S. M. *Vibrio cholerae* Iron Transport Systems: Roles of Heme and Siderophore Iron Transport in Virulence and Identification of a Gene Associated with Multiple Iron Transport Systems. *Infect. Immun.* 1994, 62, 5120-5125; Litwin, C. M.; Rayback, T. W.; Skinner, J. Role of Catechol Siderophore in *Vibrio vulnificus* Virulence. *Infect. Immun.* 1996, 64, 2834-2838 and Stelma, G. N.; Reyes, A. L.; Peeler, J. T.; Johnson, C. H.; Spaulding, P. L. Virulence Characteristics of Clinical and Environmental Isolates of *Vibrio vulnificus*. *Appl. Environ. Microbiol.* 1992, 58, 2776-2782]. For example, *Vibrio cholerae* can utilize transferrin and heme as iron sources. The issue then becomes how useful a target the siderophore transport apparatus is in antimicrobial design strategies.

Miller has, in a series of classic studies, employed siderophores and the corresponding transporters as vectors for the delivery of antibiotics [Miller, M. J.; Malouin, F. Siderophore-Mediated Drug Delivery: The Design, Synthesis, and Study of Siderophore-Antibiotic and Antifungal Conjugates. In *The Development of Iron Chelators for Clinical Use*, Bergeron, R. J.; Brittenham, G. M., Eds. CRC: Boca Raton, 1994; pp 275-306]. Alternatively, Esteve-Gassent was able to demonstrate that a vaccine developed to treat eels infected with *Vibrio vulnificus* serovar E. contained antigens to the putative receptor for vulnibactin. Esteve-Gassent point out that the antibody could be blocking siderophore uptake, could trigger classical complement activation, or "mark bacteria for opsonophagocytosis." [Esteve-Gassent, M. D.; Amaro, C. Immunogenic Antigens of the Eel Pathogen *Vibrio vulnificus* Serovar E. *Fish Shellfish Immunol.* 2004, 17, 277-291].

SUMMARY OF THE INVENTION

One embodiment of the invention relates to an immunogenic composition comprising a siderophore covalently linked to a pharmaceutically acceptable carrier molecule wherein the antigenicity of the siderophore moiety is sufficient to stimulate an immunologic response to the siderophore on a surface of a microorganism at the siderophore transporter level when the composition is circulating in the bloodstream of a human or non-human animal.

Another embodiment of the invention concerns a bacterial vaccine suitable for administration to a human or non-human animal comprising the above-described composition and a pharmaceutically acceptable carrier.

An additional embodiment of the invention comprises a method for immunizing a human or non-human animal against infection by at least one strain of bacteria, comprising administering to the animal a sufficient amount of the above-described vaccine to enhance the immune system thereof to infection; i.e., by stimulating the production of antibodies to at least one siderophore-siderophore receptor protein-complex of at least one strain of bacteria when the vaccine is circulating in the bloodstream of a human or non-human animal.

Still another embodiment of the invention relates to an article of manufacture comprising a package and, contained therein, at least one separately packaged dosage amount of the above-described immunogenic composition sufficient to stimulate production of antibodies to at least one siderophore-siderophore receptor protein-complex of at least one strain of bacteria when the composition is circulating in the bloodstream of a human or non-human animal, wherein the package is associated with instructions for administering the dosage amount to a human or non-human animal.

A further embodiment of the invention comprises an article of manufacture comprising a package and, contained in the package, at least one separately packaged dosage amount of the above-described vaccine sufficient to stimulate production of antibodies to at least one siderophore receptor protein of at least one strain of bacteria when said vaccine is circulating in the bloodstream of a human or non-human animal, wherein said package is associated with instructions for administering said dosage amount to a human or non-human animal.

BRIEF DESCRIPTION OF THE DRAWINGS

FIG. 3: competitive binding ELISA of diluted polyclonal sera (1:10,000) from mice immunized with the OVA-VIB conjugate (4). Animal M1 (FIG. 3A) was immunized with 4 twice s.c. at 50 μg/injection, while mouse M2 (FIG. 3B) was immunized with 4 twice s.c. at 100 μg/injection. The sera were incubated with varying concentrations of the OVA-VIB antigen, prior to being tested via ELISA against the BSA-VIB antigen. The dotted line indicates the amount of OVA-VIB ~0.05 μg/mL) needed to reduce the optical density of the p-nitrophenol product to 50% of that of the sera not incubated with any OVA-VIB. The closed circles indicate the optical density of unconjugated OVA (10 μg/mL). FIG. 4: competitive binding ELISA of purified mAb from 5A6-2D5 (FIG. 4A) and 2F10-1A9 (FIG. 4B). The mAb (0.11 μg protein/mL) were incubated with varying concentrations of the OVA-VIB antigen, prior to being tested via ELISA against the BSA-VIB antigen. The dotted line indicates the amount of OVA-VIB (~0.05-0.06 μg/mL) needed to reduce the optical density of the p-nitrophenol product to 50% of that of the mAb not incubated with any OVA-VIB. The closed circles indicate the optical density of unconjugated OVA (10 μg/mL).

DETAILED DESCRIPTION OF THE INVENTION

The present invention is predicated on the discovery that siderophores, as well their iron complexes, where affixed to pharmaceutically acceptable large carrier molecules, exhibit sufficient antigenicity to induce antibodies to microbial outer membrane ferrisiderophore complexes, thereby rendering them useful for immunogenic applications such as, for example, the formulation of bacterial vaccines.

The invention is illustrated by reference to the following specific, working examples. It will be understood by those skilled in the art that the invention is not strictly limited to the illustrative examples, but rather, is inclusive of variations and extrapolations therefrom which are determinable by one skilled in the art, based on the teachings herein.

Figure 2:
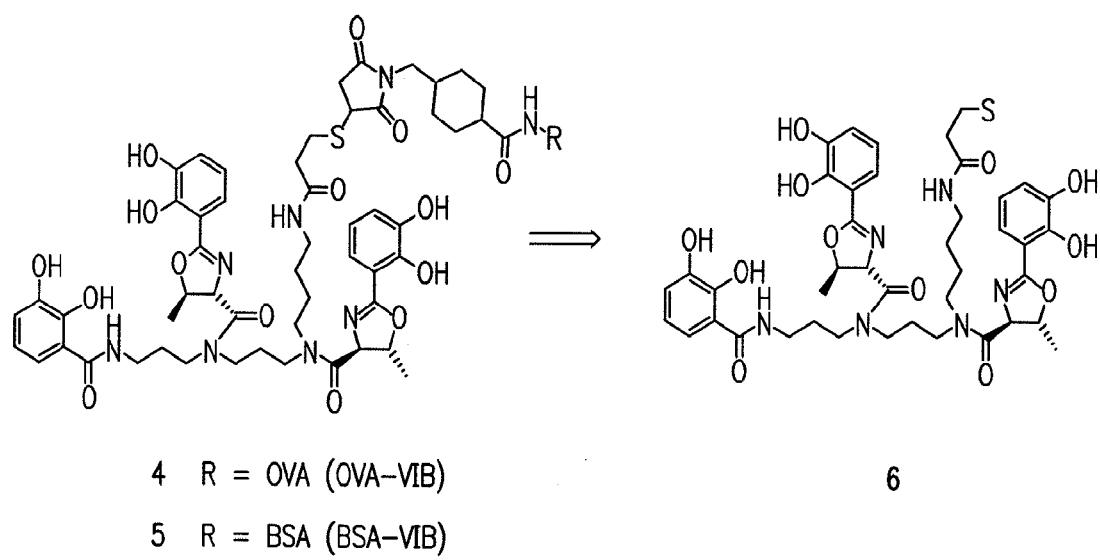

A VIB analogue, presenting with a thiol tether, 1-(2,3-dihydroxybenzoyl)-5,9-bis[[(4S,5R)-2-(2,3-dihydroxyphenyl)-4,5-dihydro-5-methyl-4-oxazolyl]carbonyl]-14-(3-mercaptopropanoyl)-1,5,9,14-tetraazatetradecane, was synthesized (FIG. 2, 6).

Figure 8:
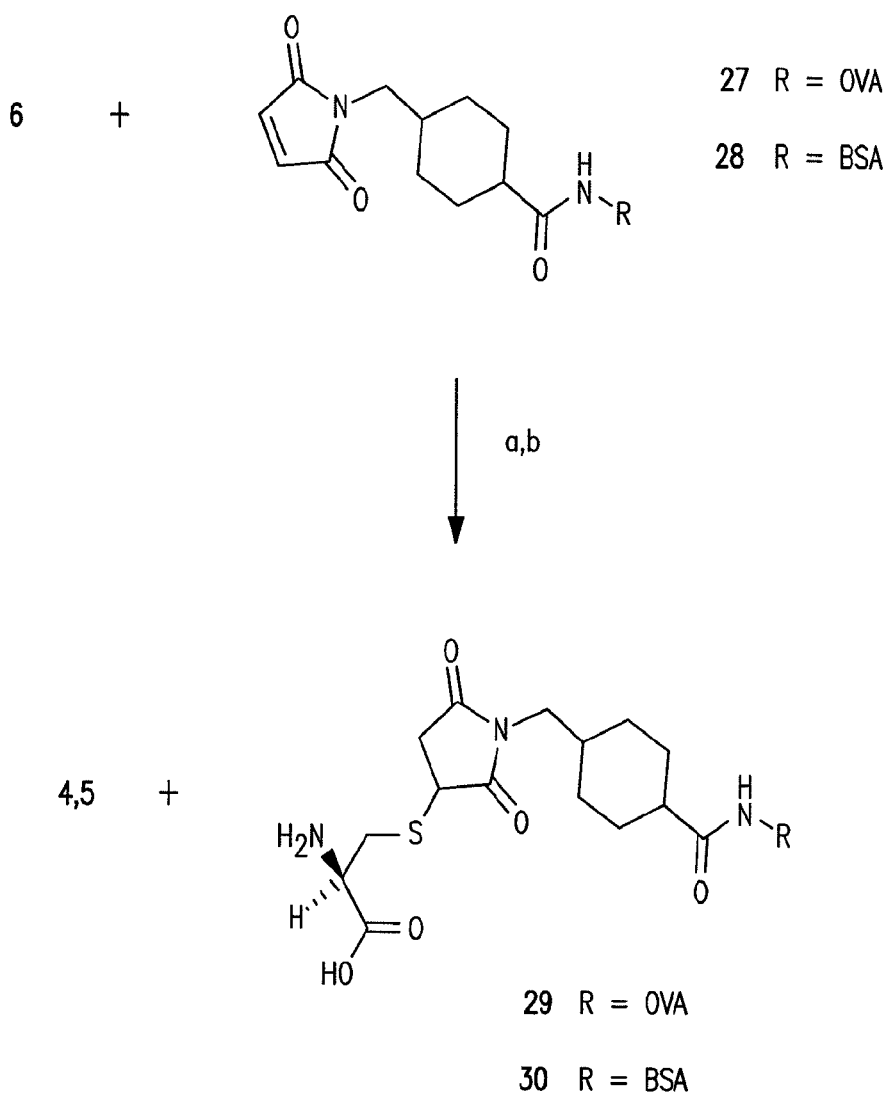

The key step in the synthesis of the vibriobactin thiol is the assembly of 1,36-bis(2,3-dihydroxybenzoyl)-15,22-dioxo-18,19-dithia-1,5,9,14,23,28,32,36-octaaza-5,9,28,32-tetrakis(L-threonyl)hexatriacontane tetrakis(trifluoroacetate) (FIG. 8, 25). The threonyl units were condensed with ethyl 2,3-dihydroxybenzimidate to generate the corresponding tetrakis(oxazoline). The resulting vibriobactin disulfide analogue was reduced to the vibriobactin thiol, and linked to both maleimide-activated ovalbumin (OVA) and bovine serum albumin (BSA).

When mice were immunized with the resulting OVA-VIB conjugate, a selective and unequivocal antigenic response to the VIB hapten was observed. The BSA-VIB conjugate was used initially for the detection of murine serum polyclonal antibodies, and ultimately IgG vibriobactin-specific monoclonal antibodies. The results are consistent with the concept that isolated adducts of siderophores covalently linked to their bacterial outer membrane receptor proteins represent credible targets for vaccine development.

There is now significant literature that supports the fact that many microorganisms present with outer membrane receptors for the binding and internalization of their ferrisiderophore complexes. It is not unreasonable, therefore to theorize that on binding to the microbial receptors, the iron siderophore complex is at least initially exposed. If sufficiently antigenic, this "ferrisiderophore face" represents a significant target in vaccine development. The antigenicity of a ferrisiderophore fixed to a large carrier molecule was determined. It was found to be very antigenic, meriting the assembly of ferrisiderophores with functionality that allow for covalent linkage to the transporter and isolation of the adduct or linking the ferrisiderophore to a C-terminal polypeptide fragment of the outer membrane receptor protein as potential vaccines. Optionally, protein adducts such as OVA- or BSA-ferrisiderophores or siderophore conjugates may be employed as vaccines.

Sufficient antigenicity of a ferrisiderophore bound to a large carrier molecule to function as a vaccine requires addressing specific issues: 1) assembling a carrier siderophore conjugate, i.e., a protein carrier conjugate, 2) raising antibodies to the conjugate in animals, and 3) assessing the antigenicity of the protein siderophore and its iron complex. Antigen Design Concept.

The examples herein focus on the generation of antibodies against vibriobactin-carrier complexes (3, VIB). The hexacoordinate iron chelator, vibriobactin, is a siderophore, responsible for iron utilization in *Vibrio cholerae* [Griffiths, G. L.; Sigel, S. P.; Payne, S. M.; Neilands, J. B. Vibriobactin, a Siderophore from *Vibrio cholerae. J. Biol. Chem.* 1984, 259, 383-385 and Payne, S. M.; Finkelstein, R. A. Siderophore Production by *Vibrio cholerae. Infect. Immun.* 1978, 20, 310-311]; however, it will be understood by those skilled in the art that the invention is equally susceptible to using any suitable siderophore; e.g., enterobactin, aureochelin, petrobactin, vulnibactin and the like.

Vibriobactin (3, VIB) is attractive for two reasons: *Vibrio cholerae* represents an important pathological target [Crosa, J. H. Signal Transduction and Transcriptional and Posttranscriptional Control of Iron-Regulated Genes in Bacteria. *Microbiol. Mol. Biol. Rev.* 1997, 61; Crosa, J. H. Molecular Genetics of Iron Transport as a Component of Bacterial Virulence. In *Iron and Infection: Molecular, Physiological, and Clinical Aspects,* 2 ed.; Bullen, J. J.; Griffiths, E., Eds. John Wiley & Sons: Chichester, UK, 1999; pp 255-288 and Litwin, C. M.; Calderwood, S. B. Role of Iron in Regulation of Virulence Genes. *Clin. Microbiol. Rev.* 1993, 6, 137-149], and critical information about vibriobactin chemistry had been established in earlier studies. Accordingly, an ovalbumin (OVA) vibriobactin protein conjugate (4, OVA-VIB) was investigated as an antigen.

A fundamental issue is to append a tether to vibriobactin (FIG. 2, 6), which would allow for fixing the ligand to a carrier protein, in this case, both OVA and bovine serum albumin (BSA). This demanded a synthetic approach very different from the assembly of vibriobactin itself. The OVA-VIB conjugate (4) would be used as an antigen to raise antibodies in mice, and the BSA-VIB conjugate (5) would be utilized in an enzyme-linked immunosorbent assay (ELISA), first for the detection of serum polyclonal antibodies, and finally, vibriobactin-specific IgG monoclonal antibodies. Thus, choosing the appropriate activated tether for the vibriobactin protein conjugate was the first hurdle. While a number of different tethers were considered (e.g., acyl, halo, thiol), previous experience with hypusine antibody generation [Bergeron, R. J.; Weimar, W. R.; Müller, R.; Zimmerman, C. 0.; McCosar, B. H.; Yao, H.; Smith, R. E. Synthesis of Reagents for the Construction of Hypusine and Deoxyhypusine Peptides and Their Application as Peptidic Antigens. *J. Med. Chem.* 1998, 41, 3888-3900] encouraged pursuit of a thiol-containing tether. The final ligand would be 1-(2,3-dihydroxybenzoyl)-5,9-bis[[(4S,5R)-2-(2,3-dihydroxyphenyl)-4,5-dihydro-5-methyl-4-oxazolyl]carbonyl]-1443-mercaptopropanoyl)-1,5,9,14-tetraazatetradecane (6), or vibriobactin thiol (FIG. 2).

Figure 6:
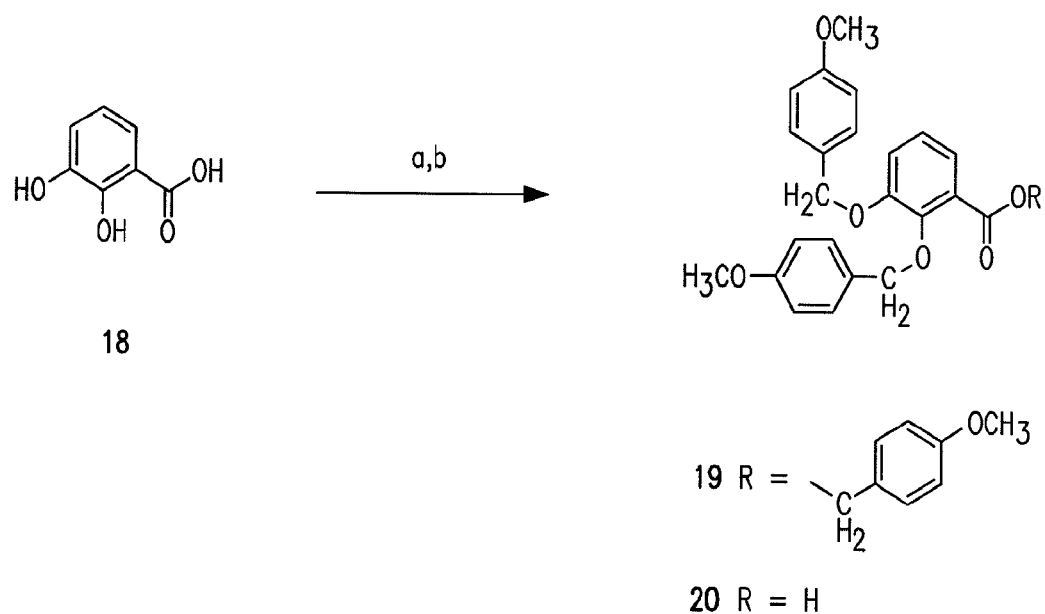
FIGS. 6-8 depict reaction schemes for synthesizing representative compounds of the invention.

A catechol protecting group other than methyl, that is, one that could be removed concurrently with the BOC functionality while leaving the disulfide intact, was required. Thus, 2,3-dihydroxybenzoic acid (18) was converted to its trianion with NaH in DMF and treated with excess 4-methoxybenzyl bromide to make ester 19 in 62% yield. Hydrolysis of 19 with NaOH (aqueous) in dioxane produced 2,3-bis(4-methoxybenzyloxy)benzoic acid (20) in 90% recrystallized yield (Scheme 1: Synthesis of $20^a$. $^a$Reagents: (a) 60% NaH, 4-methoxybenzyl bromide (3.5 equivalents), DMF, 62%; (b) 2N NaOH, dioxane, 90%). Activation of an equivalent of carboxylic acid 20 with CDI and stirring with $N^{12}$-(phthaloyl) thermospermine (12) in $CH_2Cl_2$ and $NEt_3$ afforded diamine 21 in 57% yield (FIG. 6).

Figure 7:
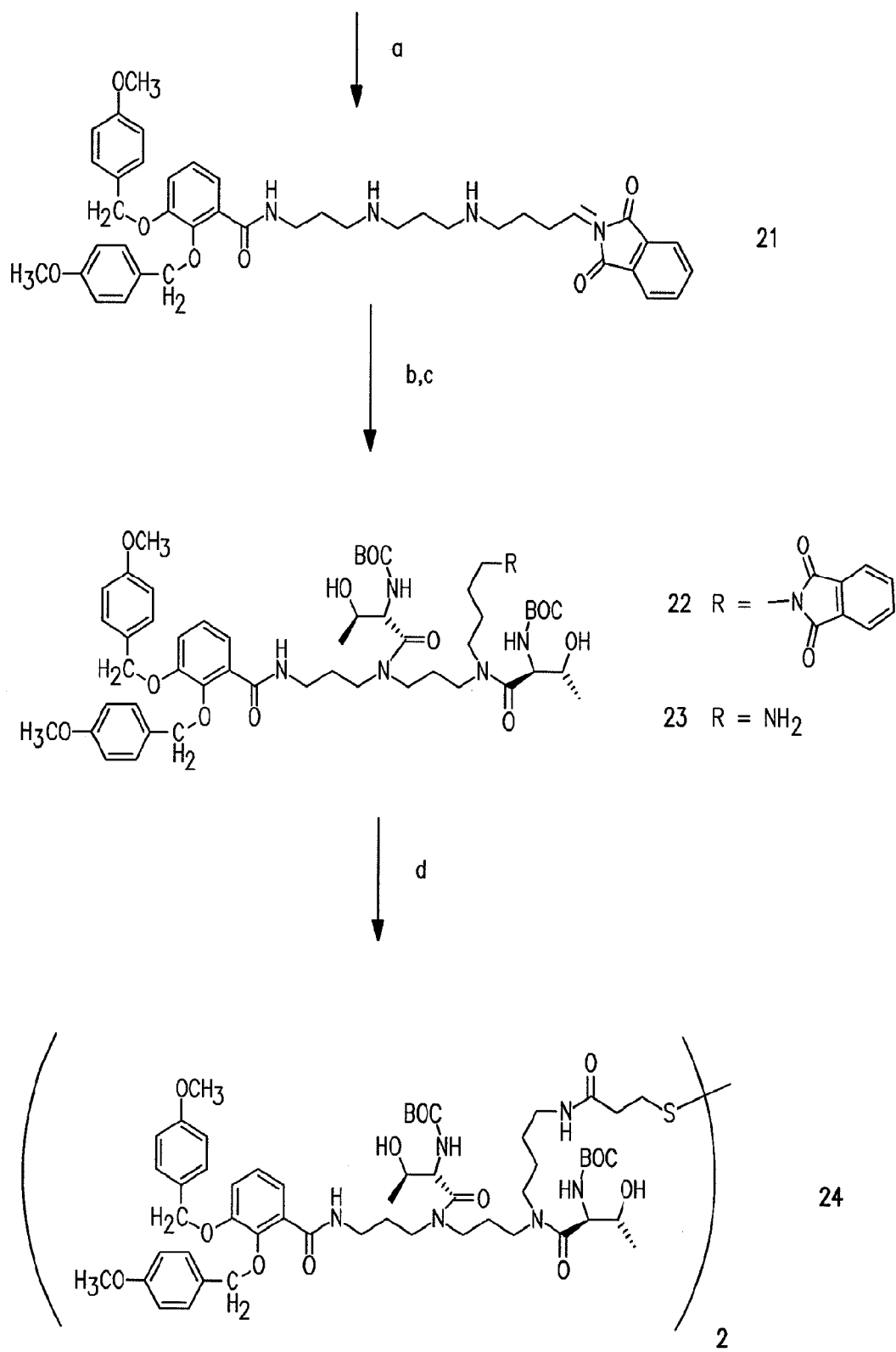
Figure 7:
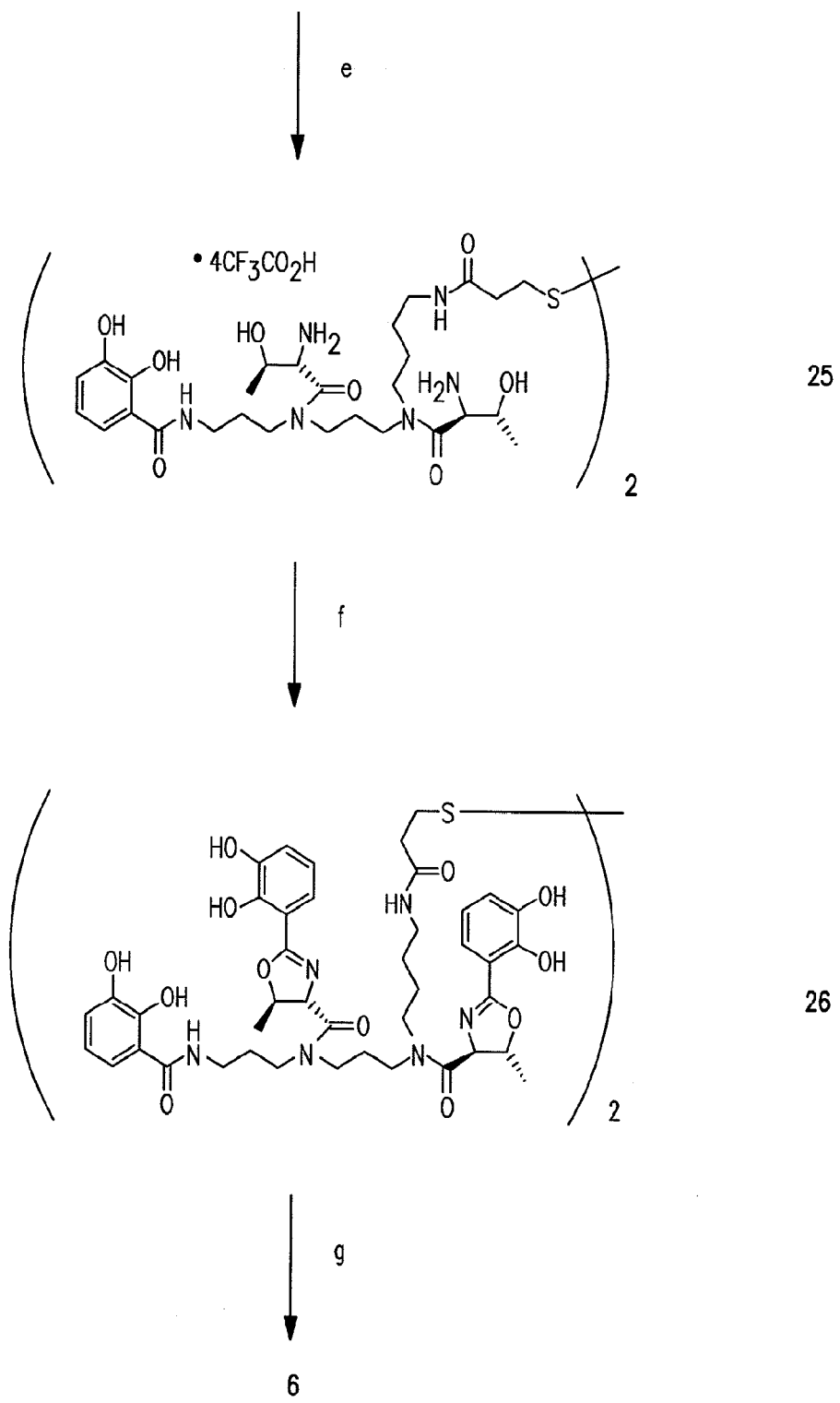

The secondary amines of 21 were acylated with the active ester of N-(BOC)-L-threonine as before to generate tetraamine derivative 22 in 60% yield. The phthalimide protecting group of 22 was removed in 90% yield with hydrazine hydrate in EtOH at room temperature, yielding intermediate 23, two equivalents of which were joined utilizing 3,3'-dithiodipropionic acid (CDI in $CH_2Cl_2$), resulting in disulfide 24 in 60% yield. The threonyl carbamates and the 4-methoxybenzyl ethers [Fletcher, S.; Gunnings, P. T. Mild, Efficient and Rapid O-Benzylation of the Ortho-Substituted Phenols with Trifluoroacetic Acid. *Tetrahedron Lett.* 2008, 49, 4817-4819] of 24 were simultaneously cleaved, using TFA in anisole and $CH_2Cl_2$; SEPHADEX LH-20 (beaded, cross-linked, hydroxypropylated dextran) purification resulted in a 60% yield of disulfide 25, a tetrakis(TFA) salt. The threonyl moieties of 25 were next condensed with excess ethyl 2,3-dihydroxybenzimidate in refluxing EtOH to produce tetrakis(oxazoline) disulfide 26 in 20% yield. Finally, disulfide iron chelator 26 was cleaved to the free thiol 6 in 60% yield, utilizing $H_2$ (3 atm) over Pd black in $CH_3OH$ under iron-free conditions (FIG. 7). Functionalization of Vibriobactin Thiol (6) with OVA and BSA Protein Carriers.

Vibriobactin thiol (6), freshly generated from disulfide 26 (FIG. 7), was incubated with a maleimide-activated OVA (27) or BSA (28) protein carrier for 8 h., resulting in Michael adduct OVA-VIB (4) or BSA-VIB (5), respectively (Scheme 2: Synthesis of vibriobactin thiol $6^a$. $^a$Reagents: (a) 20, CDI, $CH_2Cl_2$, $NEt_3$, 57%; (b) N-tert-butoxycarbonyl-L-threonine N-hydroxysuccinimide ester (2.5 equivalents), DMF, 60%; (c) hydrazine hydrate, EtOH, 90%; (d) 3,3'-dithiopropionic acid, CDI, $CH_2Cl_2$, $NEt_3$, 60%; (e) TFA, anisole, $CH_2Cl_2$, 0°→rt, 2 h, 60%; (f) ethyl 2,3-dihydroxybenzimidate, EtOH, reflux, 36 h, 20%; (g) $H_2$, 3 atm, Pd black, EtOH, 1 d, 60%).

Unreacted maleimide was capped by conjugating it further with cysteine for 8 h. Both 4 and 5 were purified on a dextran desalting column. Positive fractions, as determined by the optical density (OD) at 280 nm, were analyzed for protein concentration using a Coomassie assay [Pierce. Coomassie Plus the Better Bradford™ Assay Kit. Product No. 23236. In Rockford, Ill.]. Functionalities 29 and 30 were also generated (FIG. 8); 30 was used as a negative control in evaluating the capacity of 6 as an antigenic determinant when bound to BSA.

Iron Complexes of 4, 27, 3 and 26.

Figure 1:
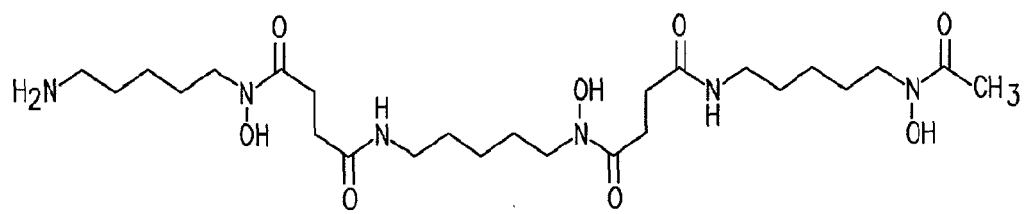
FIGS. 1, 2 and 5 depict structural formulas of various compounds identified in the application.
Figure 1:
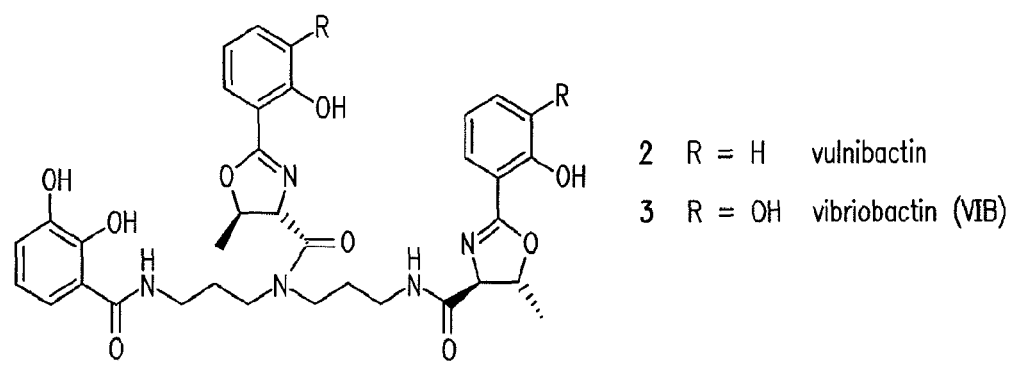

Protein desferrivibriobactin-OVA complex 4 was converted to the corresponding ferric siderophore complex 31 by mixing the conjugate with excess ferric nitrilotriacetate in phosphate buffer for 2 h. At this point, desferrioxamine (1) (FIG. 1) was added to complex excess iron. The mixture was then purified on a G-25 Sepharose column. The same ferration procedure, including purification, was carried out on the maleimide-activated OVA (27), producing ferric protein complex 32. The iron content of the purified ferrivibriobactin protein adduct (31), the iron-treated maleimide protein (32), and the elution buffer were determined by inductively coupled plasma mass spectroscopy (ICP-MS). The background iron, elution buffer iron, and maleimide protein iron were subtracted from the iron content associated with the ferrivibriobactin OVA complex (31). From this measurement, and assuming that Fe(III) and vibriobactin form a 1:1 complex, the coupling efficiency of OVA maleimide (27) to 6 was 30%.

Vibriobactin (3) and vibriobactin disulfide (26) iron(III) complexes, 33 and 34 respectively, which were to be evaluated as potential antigens, were prepared by using iron(III) acetylacetonate (2.0 equivalents) in Tris HC1 buffer, pH 7.4. The resulting suspension was separated on a small C-18 column eluting with EtOH (aqueous). Colored fractions were pooled and lyophilized.

Development of Murine Monoclonal Antibodies Against Vibriobactin.

The procedures were similar to those of Kao and Klein [Kao, K.-J.; Klein, P. A. A Monoclonal Antibody-Based Enzyme-Linked Immunosorbent Assay for Quantitation of Plasma Thrombospondin. *Am. J. Clin. Pathol.* 1986, 86, 317-323] and Simrell, et al [Simrell, C. R.; Klein, P. A. Antibody Responses of Tumor-Bearing Mice to Their Own Tumors Captured and Perpetuated as Hybridomas. *J. Immunol.* 1979, 123, 2386-2394]. Briefly, the OVA-VIB conjugate (4) was used as an antigen to raise antibodies in mice. Antigenic response was determined via an ELISA. Once an adequate IgG response was observed, an immunized mouse was given a final, prefusion booster of the antigen without adjuvant. The mouse was euthanized four days later and antibody-forming cells from the animal's spleen were fused to tumor cells grown in culture. The resulting hybridomas were screened for antibody production; antibody-producing hybridomas were cloned. Monoclonal antibodies were then produced and purified.

Polyclonal Antibody Response.

Two mice (M1 and M2) were immunized with 4. The immune response (serum titer) of these animals and non-immunized mice (normal mouse sera, NMS) was determined via ELISA for polyclonal antibodies against the following potential antigens: a) BSA-VIB conjugate (5), b) BSA-cysteine conjugate (30), c) vibriobactin thiol (6), d) vibriobactin disulfide (26), e) vibriobactin disulfide iron complex (34), f) vibriobactin (3), and g) vibriobactin iron complex (33). Twenty-three days after the second immunization, the serum from the mouse immunized with a higher dose of OVA-VIB (M2) seemed more active against the BSA-VIB antigen than M1, with a higher p-nitrophenol OD at 405 nm at all dilutions (Table 1). However, by day 56, there was little difference in the reactivity of serum from M1 vs. M2. At this time, even after a 25,600-fold dilution, the serum titers of the immunized mice against BSA-VIB were over nine times greater than that of the NMS (Table 1).

The mouse sera also contained polyclonal antibodies against BSA-cysteine that were nearly as active as antibodies against BSA-VIB (Table 1). Since cysteine was used to cap unreacted maleimide sites in the synthesis of 4, this was expected. As will be discussed below, this was not an issue for the purified monoclonal antibodies. It was still possible to select for antibodies specific against the OVA-VIB conjugate. The mouse sera did not react against any of the other antigens, c-g. This could have been attributed to a simple lack of activity in the case of antigens c-g, or the nature of the ELISA itself. Antigens c-g are relatively low molecular weight, moderately water-soluble ligands. These compounds may not have adhered to the ELISA wells, or they may have been removed during the washing steps. In order to settle this issue, a series of competitive binding ELISAs were performed.

Competitive Binding ELISA.

In the competitive binding ELISA, sera from immunized mice or non-immunized mice were first incubated with potential antigens f-g, or with OVA-VIB, at antigen concentrations ranging from 0-250 μg/mL. If an antigen is an effective competitor, it will bind to the antibody during this initial incubation, leaving less antibody available to bind to a second antigen coated on the ELISA plate. This "competition" will be reflected in lower p-nitrophenol optical density values.

Figure 3A:
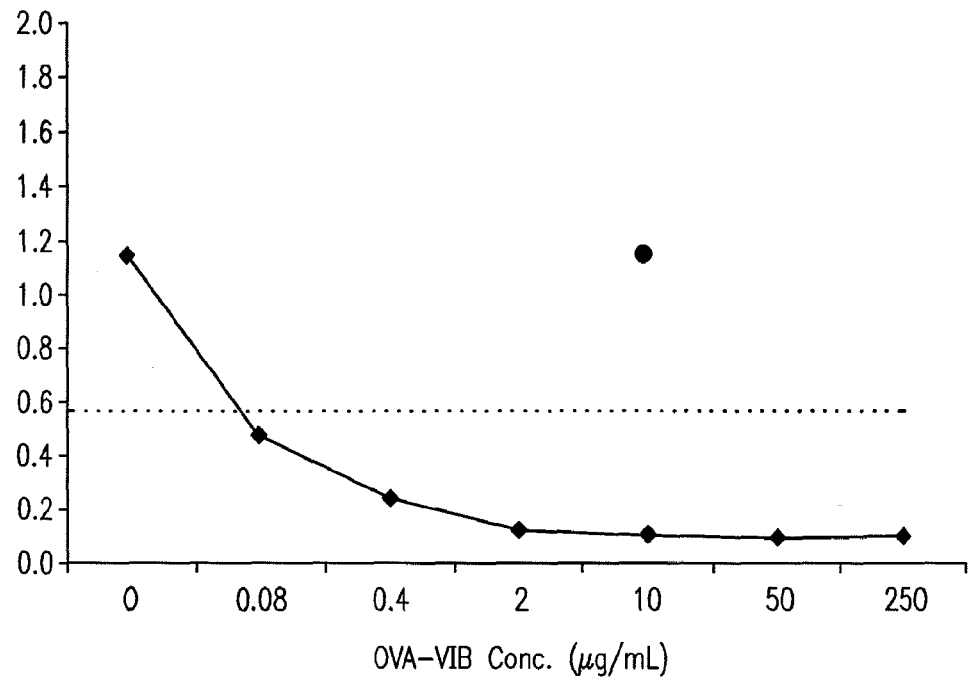
FIGS. 3 and 4 depicts competitive binding ELISA for compounds of the invention.
Figure 3B:
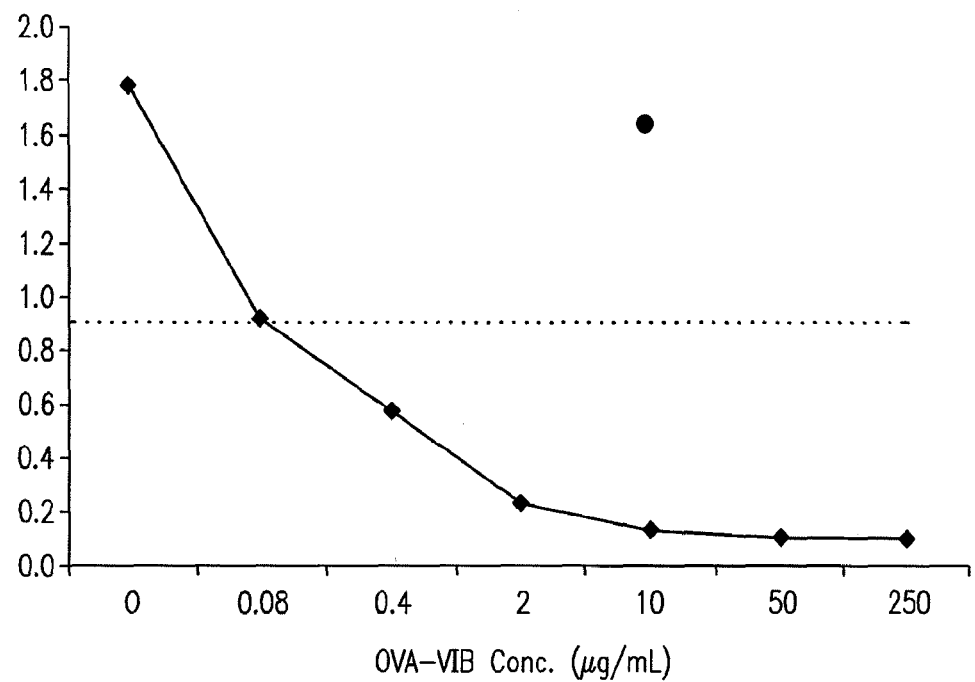

The OVA-VIB antigen was found to be an effective competitor at all concentrations tested (FIG. 3, Table 2) (FIG. 3—Competitive binding ELISA of diluted polyclonal sera (1:10,000) from mice immunized with the OVA-VIB conjugate (4)). Animal M1 (A) was immunized with 4 twice s.c. at 50 μg/injection, while mouse M2 (B) was immunized with 4 twice s.c. at 100 μg/injection. The sera were incubated with varying concentrations of the OVA-VIB antigen, prior to being tested via ELISA against the BSA-VIB antigen. The dotted line indicates the amount of OVA-VIB (~0.05 μg/mL) needed to reduce the optical density of the p-nitrophenol product to 50% of that of the sera not incubated with any OVA-VIB. The closed circles indicate the optical density of unconjugated OVA (10 μg/mL).

The smaller antigens, f-g, were not effective competitors (data not shown), verifying the necessity for a large carrier molecule in order for the antibody to recognize vibriobactin. Unconjugated OVA was not an effective competitor. The p-nitrophenol optical density of serum incubated with OVA against the BSA-VIB antigen was 92% greater than serum first incubated with OVA-VIB at the same concentration (FIG. 3). It is clear that the antibody "recognizes" the siderophore on the protein carrier.

Cell Fusion-Hybridoma Formation.

Four months after the second immunization, mouse M2 was given a prefusion booster of 4. Fusion was done following the method of Simrell, et al., except that the myeloma cell line used was Sp2/0. In short, spleen cells were fused with Sp2/0 cells such that the ratio of spleen cells to Sp2/0 cells was 7:1. After incubating for 11 days, the supernatants from the resulting hybridomas were tested via ELISA against the BSA-VIB antigen. The hybridomas that gave the strongest ELISA signal were further cultured for 7 days. Their supernatants were tested again via ELISA against BSA-VIB, BSA-VIB-iron, and BSA-cysteine. The class of antibody (IgG or IgM) was also determined. The twelve most active hybridomas that were BSA-VIB and BSA-VIB-iron positive and BSA-cysteine negative are shown in Table 3. One hybridoma, 2D6, was IgM-positive; the remaining eleven hybridomas were IgG-positive (Table 3). Two of the most promising IgG-positive hybridomas, 5A6 and 2F10, were cloned.

Cloning of Antibody-producing Hybridomas.

Cells from the 5A6 and 2F10 hybridomas were diluted to a concentration of one or two cells per well. After incubating for four days, the plates were scanned microscopically and were scored for single colony and multiple colony wells. Ten days after seeding, supernatant from the wells that contained cells underwent screening via ELISA against BSA-VIB. Supernatants from the single colony wells of 5A6 were not very active against BSA-VIB (data not shown). Because of this, the four most BSA-VIB positive multiple colony wells of 5A6 were pooled, diluted, and replated as single cells. Ten days later, supernatants from the resulting clones were tested by an ELISA against BSA-VIB. The ten single colony wells with the strongest ELISA positives (primary) against BSA-VIB are shown in Table 4. After incubating for an additional 5 days, the supernatants were tested again (secondary) via ELISA against BSA-VIB, BSA-VIB-iron and BSA-cysteine. All ten clones were highly active against BSA-VIB and BSA-VIB-iron and showed little activity towards BSA-cysteine (Table 4). A positive BSA-VIB and BSA-VIB-iron response and a negligible BSA-cysteine response were a clear indication that the antigenic determinants of the antibody were associated with the vibriobactin segment of the BSA-VIB conjugate, and not to BSA itself.

Recloning of the 2F10 hybridoma was unnecessary: 2F10-1A9 and 2F10-2A3 were highly active against BSA-VIB and BSA-VIB-iron and poorly responsive to BSA-cysteine (Table 5). These two clones, as well as two clones from 5A6 (5A6-2D5 and 5A6-1G8), were selected for further evaluation. The clone supernatants were assayed for the class of antibody, IgG or IgM, and were shown to be IgG-positive (Table 5). Multiple stocks from each cell line were frozen. 5A6-1G8 and 2F10-2A3 were tested for mycoplasma contamination and were found to be negative. Additional monoclonal antibodies (mAb) derived from 5A6-2D5 and 2F10-1A9 were produced and purified.

Competitive Binding ELISA Studies: Determination of the Sensitivity of the Purified Monoclonal Antibodies.

Figure 4A:
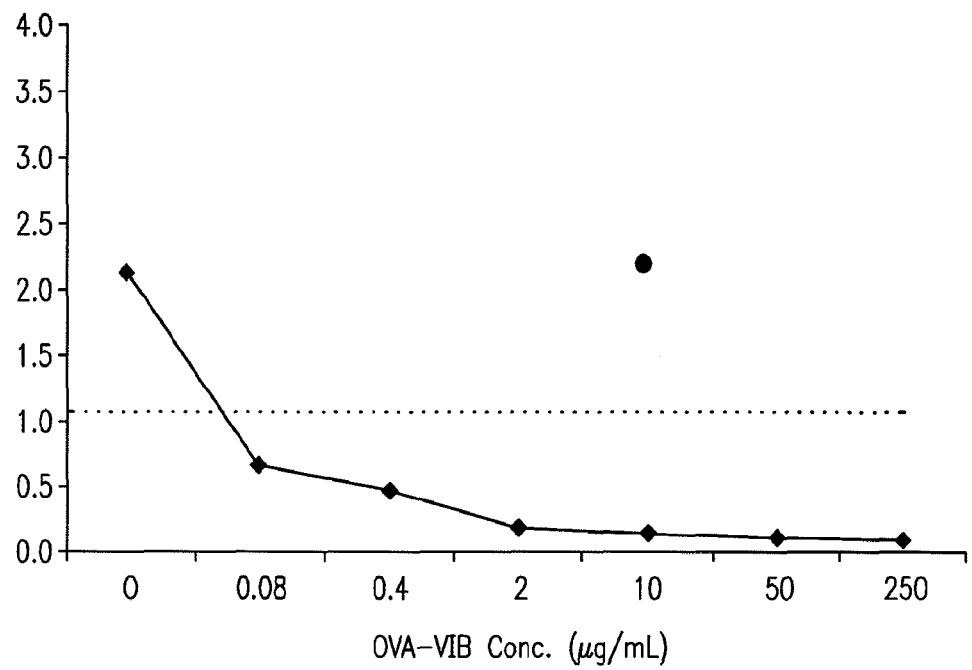
Figure 4B:
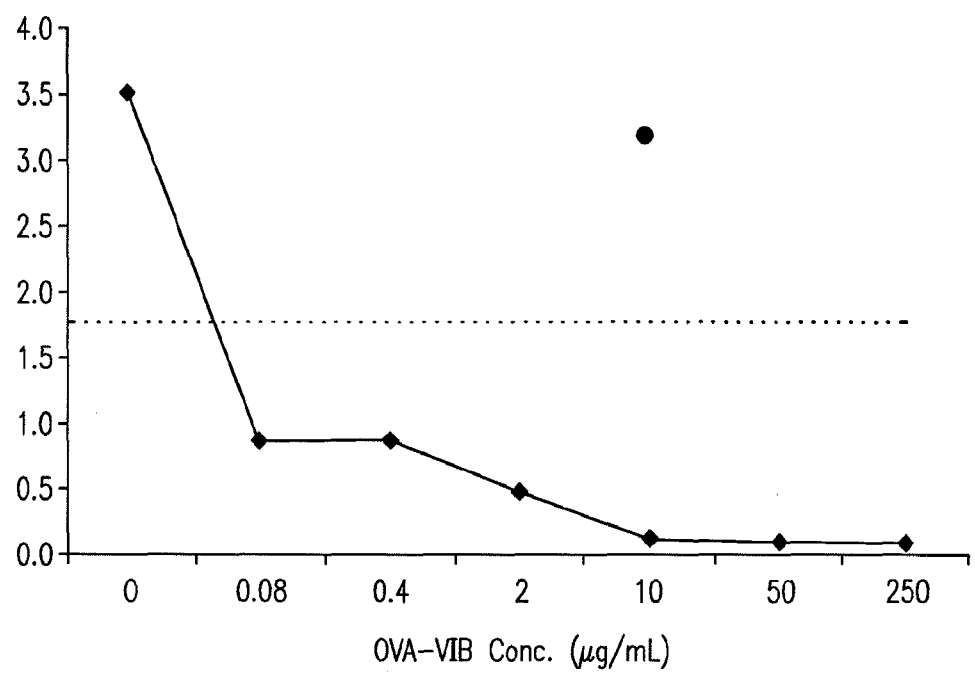
Figure 5:
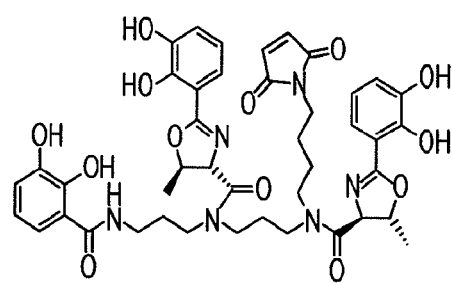

Competitive binding ELISA studies using the purified mAb were conducted. The mAb were first incubated with varying concentrations of the OVA-VIB antigen, from 0-250 μg/mL, prior to being transferred to an ELISA plate that had been coated with the BSA-VIB antigen. The OVA-VIB antigen was found to be an effective competitor at all concentrations tested (FIG. 4, Table 6) (FIG. 4: Competitive binding ELISA of purified mAb from 5A6-2D5 (A) and 2F10-1A9 (B). The mAb (0.11 μg protein/mL) were incubated with varying concentrations of the OVA-VIB antigen, prior to being tested via ELISA against the BSA-VIB antigen. The dotted line indicates the amount of OVA-VIB (~0.05-0.06 μg/mL) needed to reduce the optical density of the p-nitrophenol product to 50% of that of the mAb not incubated with any OVA-VIB. The closed circles indicate the optical density of unconjugated OVA (10 μg/mL).)

Unconjugated OVA was not an effective competitor. The p-nitrophenol optical density of the mAb initially incubated with OVA against the BSA-VIB antigen were approximately 90% greater than those of the mAb first incubated with OVA-VIB at the same concentration (Table 6). It is clear that the antibody "recognizes" the siderophore on the protein carrier.

Antigenic Determinants.

One of the observations that stands out with the data from the antibody-containing hybridoma supernatants is the lack of difference in reactivity between BSA-VIB and the corresponding BSA-VIB-iron complex (Table 3, Table 5). There are profound differences in structure between vibriobactin and its iron complex. The 1:1 vibriobactin iron complex would have all of the donor groups, (e.g., aromatic hydroxyls and oxazoline nitrogen) folded into the metal. Catecholamides such as vibriobactin bind iron very tightly, with formation constants of nearly $10^{48}$ M$^{-1}$. This means that, because of the ubiquitous nature of iron, the OVA-VIB- and BSA-VIB-iron complexes were probably formed in vitro. In fact, it is likely that antibodies in animals are being formed against the OVA-VIB iron complex.

To support this idea, bile duct-cannulated rats were given vibriobactin (3) subcutaneously (s.c.) at a dose of 75 µmol/kg. The rodents' bile and urine were collected for 48 h to determine if vibriobactin sequestered and promoted the excretion of iron. The iron content of the bile and urine were determined using atomic absorption spectroscopy. This model has been used for many years to evaluate the efficiency with which iron chelators promote the excretion of iron from animals [Bergeron, R. J.; Streiff, R. R.; Creary, E. A.; Daniels, R. D., Jr.; King, W.; Luchetta, G.; Wiegand, J.; Moerker, T.; Peter, H. H. A Comparative Study of the Iron-Clearing Properties of Desferrithiocin Analogues with Desferrioxamine B in a Cebus Monkey Model. *Blood* 1993, 81, 2166-2173 and Bergeron, R. J.; Streiff, R. R.; Wiegand, J.; Vinson, J. R. T.; Luchetta, G.; Evans, K. M.; Peter, H.; Jenny, H.-B. A Comparative Evaluation of Iron Clearance Models. *Ann. N. Y Acad. Sci.* 1990, 612, 378-393]. Vibriobactin was indeed found to sequester iron in vivo. Compound 3 forms a tight 1:1 iron complex with Fe(III). Rats given 75 µmol/kg of 3 would be expected to clear 75 µg-atoms/kg of iron if the binding and clearance were 100% efficient. However, the iron clearing efficiency of 3 in the rats, i.e., the actual amount of iron cleared by the ligand vs. the theoretical iron clearance, was only 4.3±1.1%. This implied that up to 95% of the free ligand remains, or is cleared uncomplexed. In the bile duct-cannulated rats this, of course, all unfolds in a matter of hours. However, in the mouse immunization experiments, the OVA-VIB conjugate had weeks to become saturated with iron; the most important issue is the iron to ligand ratio. Assuming that 3.23 µg-atoms of iron/kg is available for chelation, in a 25 g mouse $1.45 \times 10^{-9}$ moles of iron is available. The mice were effectively given $0.33 \times 10^{-9}$ (M1) or $0.66 \times 10^{-9}$ (M2) moles of vibriobactin conjugated to OVA. In view of the protracted exposure of the ligand to iron, it is difficult to imagine that all of the vibriobactin bound to OVA would not also be iron-bound.

It will be understood by those skilled in the art that various methodologies for assembling antigens that would allow for the assessment of the antigenic properties of vibriobactin fixed to large carrier molecules, e.g., OVA and BSA may be employed in the practice of the invention. In the examples herein, a thiol analogue was chosen, 1-(2,3-dihydroxybenzoyl)-5,9-bis[[(4S,5R)-2-(2,3-dihydroxyphenyl)-4,5-dihydro-5-methyl-4-oxazolyl]carbonyl]-14-(3-mercaptopropanoyl)-1,5,9,14-tetraazatetradecane (6), or vibriobactin thiol (FIG. 2). Other tethers such as amines, carboxylic acids, halides, tosylates, alkylating agents and the like may also be used.

In the synthesis approach, a catechol protecting group was employed in 2,3-bis(4-methoxybenzyloxy)benzoic acid (20). This could be removed concurrently with the BOC functionality of the key intermediate 24 to produce 25, while leaving the requisite disulfide intact. The threonyl moieties of 25 were next condensed with excess ethyl 2,3-dihydroxybenzimidate. Finally, disulfide iron chelator 26 was cleaved to the vibriobactin thiol (6), utilizing $H_2$ (3 atm) over Pd black in $CH_3OH$ under iron-free conditions. The thiol (6) was then incubated with a maleimide-activated OVA (27) or BSA (28) protein carrier, resulting in Michael adduct OVA-VIB (4) or BSA-VIB (5), respectively. The OVA-VIB conjugate was mixed with an adjuvant and was successfully used as an antigen to raise antibodies in mice, and the BSA-VIB conjugate was used in an ELISA, first for the detection of serum polyclonal antibodies, and ultimately vibriobactin-specific IgG monoclonal antibodies.

These results are consistent with the idea that siderophores, such as vibriobactin, present with strong antigenic determinants when fixed to a large carrier molecule. The data are in keeping with the idea that covalently linking siderophore analogues to the bacterial outer membrane receptors represents a target for vaccine development. When isolated and injected into animals these siderophore "outer membrane receptor" adducts induce antibody formation, selecting for the ferrisiderophore face. Animals immunized with, for example, the ferrivibriobactin outer membrane adduct and then exposed to *Vibrio cholerae* would clear the microorganism by complement activation and opsonophagocytosis.

Alternatively, the appropriate siderophore could be affixed to a C-terminal polypeptide fragment of the siderophore outer membrane receptor protein. These C-terminal fragments have already been identified for a number of siderophore outer membrane receptor proteins. The siderophore/polypeptide fragment complex or the siderophore affixed to a large peptide such as OVA or BSA may also be employed as vaccines.

EXAMPLES

Biological Materials and Methods

The animal-related protocols were approved by the University of Florida Institutional Animal Care and Use Committee. Two female Balb/c ByJ mice (6-7 weeks old) were purchased from The Jackson Laboratory (Bar Harbor, Me.). TITERMAX (a water-in-oil emulsion of squalene, sorbitan monooleate 80, a block copolymer, and microparticulate silica) Adjuvant was obtained from Sigma (St. Louis, Mo.). ELISA plates (MAXISORP) (high protein-binding capacity polystyrene multi-well ELISA plates)) were purchased from Nalge Nunc International Co. (Naperville, Ill.). An automatic microplate washer (Model EL404, Bio-Tek Instruments, Inc., Winooski, Vt.) and microplate reader (Spectromax Plus 384, Molecular Devices, Union City, Calif.) were utilized. The rabbit anti-mouse IgG (whole molecule), goat anti-mouse IgG (γ-chain specific) and goat anti-mouse IgM (µ-chain specific) antibodies were purchased from Sigma (St. Louis, Mo.). Dulbecco's Modified Eagle's Medium (HyClone) was obtained from Thermo Fisher Scientific (Waltham, Mass.). Hybridoma plates were incubated in a Forma Scientific Incubator, Model 3154 (Marietta, Ga.). A MYCOALERT Kit (a biochemical test based on the activity of mycoplasmal enzymes) (Lonza, Allendale, N.J.) was used to assess potential mycoplasma contamination. Monoclonal antibodies were produced using hybridoma production media, BD Cell Mab Medium, Quantum Yield, (BD Biosciences, San Jose, Calif.) supplemented with 10% low IgG fetal bovine serum (HyClone, Thermo Fisher Scientific, Waltham, Mass.) in CEL-Line CL 350 flasks (Sartorius Stedim, New York, N.Y.). Amicon Ultra-15 centrifugal filters with a 30 kDa cut-off were obtained from Millipore (Billerica, Mass.). Male Sprague-Dawley rats (400-450 g) were procured from Harlan Sprague-Dawley (Indianapolis, Ind.). CREMOPHOR RH-40 (polyoxyl 40 hydrogenated castor oil) was provided by BASF (Parsippany, N.J.). An atomic absorption spectrometer, Perkin-Elmer model 5100 PC (Norwalk, Conn.), was used to determine the iron content of the rat bile and urine samples.

Monoclonal Antibody Production: Immunization.

To produce antibodies to small molecules in animals, conjugation to larger carrier proteins (e.g., OVA or BSA) is generally required. The vibriobactin thiol (6) was conjugated with OVA using a linker (27) to prepare the OVA-VIB conjugate (4), which was mixed with an adjuvant and used as an antigen to immunize two mice. One mouse (M1) received 50 µg of 4 per s.c. injection and the other mouse (M2) received 100 µg of 4 per s.c. injection. The mice were given a second immunization of 4 at the same doses four weeks later.

Non-competitive Binding ELISA Procedure.

The method followed the approach of Kao and Klein. Briefly, the assay involved coating a potential antigen (50 µL/well) on the ELISA plates, utilizing solutions of antigens ranging in concentration from 1-40 µg/mL. The antigens: a) BSA-VIB conjugate (5), b) BSA-cysteine conjugate (30), c) vibriobactin thiol (6), d) vibriobactin disulfide (26), e) vibriobactin disulfide iron complex (34), f) vibriobactin (3), and g) vibriobactin iron complex (33) were diluted in blocking buffer (1% BSA in PBS with 0.02% azide). Normal mouse sera (NMS) or medium served as negative controls. Polyclonal serum from an immunized mouse (M2) in a 1:1,000 dilution or hybridoma supernatant (Table 4, Table 5) were used as positive controls.

The plates were allowed to incubate overnight at 4° C. An ELISA wash buffer (EWB) containing PBS with 0.02% azide and 0.5% TWEEN-20 (polyoxyethylene (20) sorbitan monolaurate) was used to wash the plates. The plates were washed 4 times (300 µL/wash) using an automatic microplate washer. The wells were then blocked with 1% BSA in PBS with 0.2% azide for 1 h at room temperature and washed again. Fifty microliters of diluted polyclonal mouse serum (1:200-1:25,600), undiluted hybridoma supernatant, or purified mAb (0.11 µg protein/mL) were added to each well. The plates for this and each subsequent step of the ELISA were incubated with gentle agitation for 1 h at room temperature. The plates were then washed 4 times as above and rabbit anti-mouse IgG (whole molecule), conjugated to alkaline phosphatase, was added (50 µL/well); the IgG antibody was diluted (1:1000) in BSA-blocking buffer. The plates were washed 4 times as above and p-nitrophenyl phosphate at a concentration of 1.0 mg/mL, 100 µL/well was added. The plates were read using an ELISA plate reader at 405 nm, tracking the absorbance (OD) of the yellow water-soluble product, p-nitrophenol. A positive response was considered a test well with a p-nitrophenol OD value three times greater than that of the negative control.

The class of antibody (IgG or IgM) of the hybridoma supernatant (Table 3) or the clone supernatant (Table 5) was determined by an ELISA, replacing the rabbit anti-mouse IgG (whole molecule) with goat anti-mouse IgG (γ-chain specific) or goat anti-mouse IgM (µ-chain specific) at a dilution of 1:4,000 (50 µL/well).

Competitive Binding ELISA Procedure.

Competitive binding ELISAs were performed on 1) serum from immunized mice that contained polyclonal antibodies, and 2) purified mAb derived from the cloning of 5A6-2D5 and 2F10-1A9. Medium was used as a negative control, while unconjugated OVA (10 µg/mL, 50 µL/well) served as a positive control for the competitive binding ELISA of the polyclonal serum (Table 2) and purified mAb (Table 6). Two types of plates were utilized: a conical bottom polypropylene plate was used for the incubation of the antibody-antigen mixture, whereas a 96-well MAXISORP (a high protein-binding capacity polystyrene multi-well ELISA plate) plate was used for the ELISA.

In brief, the polypropylene incubation plate was blocked with 300 µL of blocking buffer (1% BSA in PBS with 0.02% azide) and was allowed to incubate overnight at 4° C. The following day, the blocking buffer was removed (flicked) from the plate, and the plate was blotted on a paper towel. A 96-well ELISA plate was coated with the BSA-VIB antigen (10 µg/mL, 50 µL/well) that had been diluted in PBS with 0.02% azide. After incubating overnight at 4° C., the plate was washed 4 times (300 µL/wash) as described above, blocked with 300 µL of blocking buffer for 1 h, and washed again.

The OVA-VIB antigen was diluted in blocking buffer in micro centrifuge tubes at antigen concentrations ranging from 0-250 µg/mL. The diluted antigens (50 µL/well) were transferred from the micro centrifuge tubes to the polypropylene incubation plate that had been blocked and washed. Fifty microliters of the diluted polyclonal mouse serum (1:10,000 dilution) or mAb (0.11 µg protein/mL) were added to the incubation plate wells containing the diluted OVA-VIB antigen. The polypropylene plate was then incubated on a rocking platform for 2 h at room temperature, allowing time for the antigen-antibody complexes to form.

A portion of the antigen/antibody mixture (50 µL) was transferred from the polypropylene incubation plate to the BSA-VIB-coated ELISA plate that had been blocked and washed. The ELISA plate was incubated with gentle agitation for 1 h at room temperature and was washed 4 times with the EWB. Rabbit anti-mouse IgG antibodies conjugated to alkaline phosphatase were added (50 µL/well); the IgG antibody was diluted (1:1000) in 1% BSA-blocking buffer. After 1 h, the ELISA plate was washed four times with the EWB to remove any unreacted IgG antibodies. p-Nitrophenyl phosphate substrate (1.0 mg/mL, 100 µL/well) was added. The ELISA plate was allowed to incubate with gentle agitation for 1 h at room temperature and was read at 405 nm, tracking the OD of the yellow water-soluble product, p-nitrophenol. A positive response was considered a test well with a p-nitrophenol OD value three times greater than the negative control.

Cell Fusion-Hybridoma Formation.

Four months after the second immunization, four days before fusion, a mouse (M2) was given a prefusion booster of 100 µg of 4 without adjuvant. This final immunization was given intraperitoneally (i.p.) On the day of fusion, the mouse was anesthetized, exsanguinated and euthanized. The spleen was removed and washed with Dulbecco's Modified Eagle's Medium to remove the antibody-forming cells. The medium was supplemented with 10% equine serum and 1× antibiotic-antimycotic (per mL: 100 I.U. penicillin, 0.10 mg streptomycin, 0.25 µg amphotericin B and 50 µg gentamycin). The fusion was performed by the procedures described in Simrell, et al., except that the myeloma cell line used was Sp2/0 (a murine myeloma aminopterin-resistant cell line with a defect in purine metabolism). Spleen cells were mixed with myeloma cells at a 7:1 ratio. The fusion was performed with 50% polyethylene glycol 1500 followed by a controlled dilution with media. A centrifugation step (1500-1800 rpm for 8 minutes) was performed to pellet the fused cells. The pellet was resuspended in Dulbecco's Modified Eagle's Medium-high glucose, supplemented with 20% equine serum, 25% Sp2/0 myeloma conditioned medium and 1×hypoxanthine, aminopterin, thymidine (HAT) and was seeded in five 96-well plates at $2.8 \times 10^5$ cells per well. The plates were incubated at 37° C., with a $CO_2$ concentration of 7%.

Eleven days post-fusion, supernatants from the resulting HAT-resistant hybridomas were subjected to a primary ELISA screening to detect if the cells were secreting antibodies against BSA-VIB. Cells from fifty-one wells that were positive in the primary screening against BSA-VIB were transferred to three 24-well plates and further incubated. The supernatant was assessed again one week later in a secondary ELISA screening against BSA-VIB, BSA-VIB-iron, and BSA-cysteine (Table 3). The hybridomas that were BSA-VIB and BSA-VIB-iron positive and BSA-cysteine negative were further tested as described above to determine the class of antibody, IgG or IgM (Table 3).

Cloning of Antibody-producing Hybridomas.

Two of the most promising hybridomas, 5A6 and 2F10, were cloned. Cells from the hybridomas were diluted to a concentration of one or two cells per well and were seeded in eight 96-well plates (four plates each for 5A6 and 2F10) over a feeder layer of irradiated 3T3 mouse fibroblasts. After incubating for four days, the plates were scanned microscopically and were scored for single colony and multiple colony wells. For the 5A6 cell line, 96 single colony wells and 60 multiple colony wells were found, whereas the 2F10 cell line presented 120 single colony wells and 47 multiple colony wells. Ten days after seeding, the supernatants from all 323 wells that contained cells underwent screening via ELISA against BSA-VIB.

Supernatant from the single colony wells of 5A6 were not very active against BSA-VIB. Because of this, the four most BSA-VIB positive multiple colony wells of 5A6 were pooled, diluted, and replated as single cells in four 96-well plates. Ten days after this recloning, the ten single colony wells with the strongest ELISA positives (primary) against BSA-VIB were chosen (Table 4) and cultured in a 24-well plate. After incubating for an additional 5 days, the supernatant was tested again (secondary) via ELISA against BSA-VIB, BSA-VIB-iron and BSA-cysteine. All ten clones were highly active against BSA-VIB and BSA-VIB-iron and showed little activity towards BSA-cysteine (Table 4).

Recloning of the 2F10 hybridoma was unnecessary. The ten single colony wells with the strongest ELISA response against BSA-VIB from the four 96-well plates were transferred to a 24-well plate. After incubating for an additional 5 days, the supernatants were tested against BSA-VIB, BSA-VIB-iron and BSA-cysteine. Two clones (2F10-1A9 and 2F10-2A3), as well as two clones from 5A6 (5A6-2D5 and 5A6-1G8), were chosen for further evaluation. All four sets of clones were BSA-VIB and BSA-VIB-iron positive, poorly responsive to BSA-cysteine, and IgG-positive (Table 5). Multiple stocks from each of the four cell lines were frozen. 5A6-1G8 and 2F10-2A3 were tested for mycoplasma contamination and were found to be negative. Additional monoclonal antibodies derived from 5A6-2D5 and 2F10-1A9 were produced and purified.

Production and Purification of Monoclonal Antibodies.

5A6-2D5 or 2F10-1A9 cloned hybridoma cells were grown in hybridoma production media supplemented with 10% low IgG fetal bovine serum in CELLine CL 350 flasks. The flasks were incubated at 37° C., with a $CO_2$ concentration of 7%. One harvest per week was taken for three weeks. The cells were centrifuged at 2,000 rpm for 15 min and the resulting supernatant was collected and purified by circulating through a 5 mL Protein G Sepharose 4B column. The supernatant recirculated through the column for 90 min (~23 passes). The column was then rinsed with PBS (70-150 mL). The antibodies were eluted using 0.1 M glycine, pH 2.8. Ten fractions of 3 mL each were collected. The eluted fractions were neutralized with 2.0 M Tris, pH 9.0. Absorbance was measured at 280 nm. Fractions with the highest absorbance readings were pooled, desalted, and concentrated using Amicon Ultra-15 centrifugal filters with a 30 kDa cut-off. The concentrated, purified monoclonal antibodies were recovered in a final volume of 0.6 mL in PBS. The protein concentration of the purified mAb were measured spectrophotometrically at 280 nm. Most animalian antibodies (i.e., immunoglobulins) have protein extinction coefficients ($\epsilon_{percent}$) in the range of 12 to 15 [Thermo Fisher Scientific. Extinction Coefficients. www.piercenet.com/files/TR0006dh5-Extinction-coefficients.pdf]. The final protein concentration of the purified IgG antibody was estimated assuming a protein extinction coefficient of 14. For an IgG antibody with a molecular weight of approximately 150,000, this corresponds to a molar extinction coefficient ($\epsilon$) of 210,000 $M^{-1}$ $cm^{-1}$.

Iron Clearance in Non-Iron-Overloaded, Bile-duct Cannulated Rats.

Four rats were subjected to bile duct-cannulation as previously described. The rats were given 3 s.c. at a dose of 75 μmol/kg. The drug was solubilized in 40% CREMOPHOR RH-40 (polyoxyl 40 hydrogenated castor oil)/water. Bile samples were collected from the rats at 3 h intervals for 48 h. The urine samples were taken at 24 h intervals. Sample collection and handling are as previously described. The iron content of the bile and urine were assessed by atomic absorption spectroscopy. Iron clearing efficiency was calculated as set forth elsewhere [Bergeron, R. J.; Wiegand, J.; McManis, J. S.; McCosar, B. H.; Weimar, W. R.; Brittenham, G. M.; Smith, R. E. Effects of C-4 Stereochemistry and C-4' Hydroxylation on the Iron Clearing Efficiency and Toxicity of Desferrithiocin Analogues. *J. Med. Chem.* 1999, 42, 2432-2440]. The theoretical iron output of the chelator was generated on the basis of a 1:1 vibriobactin:iron complex.

Reagents were purchased from Aldrich Chemical Co. (Milwaukee, Wis.), and Fisher Optima-grade solvents were routinely used and DMF was distilled. Organic extracts were dried with sodium sulfate and then filtered. Distilled solvents and glassware that had been presoaked in 3N HCl for 15 min were employed in reactions involving chelators. Silica gel 70-230 from Fisher Scientific was utilized for column chromatography, and silica gel 40-63 from SiliCycle, Inc. (Quebec City, Quebec, Canada) was used for flash column chromatography. SEPHADEX LH-20 (beaded, cross-linked, hydroxypropylated dextran) was obtained from Amersham Biosciences (Piscataway, N.J.). An ICP-MS X 0675, manufactured by Thermo Electron Corporation (England), was used for the determination of the iron content of selected solutions/compounds. Derivatized OVA or BSA protein containing maleimide moieties were obtained from Pierce (Rockford, Ill.). NMR spectra were obtained at 400 MHz ($^1H$) or 100 MHz ($^{13}C$) on a Varian Mercury-400BB. Chemical shifts (δ) for $^1H$ spectra are given in parts per million downfield from tetramethylsilane for organic solvents ($CDCl_3$ not indicated) or sodium 3-(trimethylsilyl)propionate-2,2,3,3-$d_4$ for $D_2O$. Chemical shifts (δ) for $^{13}C$ spectra are given in parts per million referenced to 1,4-dioxane (δ 67.19) in $D_2O$ or to the residual solvent resonance in $CDCl_3$ (δ77.16). Coupling constants (J) are in hertz. The base peaks are reported for the ESI-FTICR mass spectra. Elemental analyses were performed by Atlantic Microlabs (Norcross, Ga.).

OVA-VIB (4) and BSA-VIB (5).

Derivatized proteins 27 [Pierce. Imject® Maleimide Activated BSA and OVA Kit Instructions. Product No. 77112, 77113. In Rockford, Ill.] or 28 [Pierce. Imject® Maleimide Activated BSA and OVA Kit Instructions. Product No. 77112, 77113. In Rockford, Ill.] (2 mg each) were dissolved in 100 μL of the conjugation buffer and incubated with a freshly prepared solution of 6 (2 mg in 200 μL of 50% aqueous DMSO) for 8 h. Unreacted maleimide was capped by conjugating it further with cysteine (2 mg in 50 μL degassed water) for 8 h. After incubation, 4 and 5 respectively were purified on a dextran desalting column (5 mL), eluting with 30% DMSO/purification buffer. Fractions (0.5 mL) were collected and the OD was measured at 280 nm. Positive fractions of each conjugate were pooled, and the protein concentration of each conjugate was estimated by a Coomassie assay.

1-(2,3-Dihydroxybenzoyl)-5,9-bis[[R4S,5R)-2-(2,3-dihydroxyphenyl)-4,5-dihydro-5-methyl-4-oxazolyl]carbonyl]-14-(3-mercaptopropanoyl)-1,5,9,14-tetraazatetradecane (6)

Palladium black (127 mg) was added to a solution of 26 (0.231 g, 0.133 mmol) in anhydrous degassed EtOH (5 mL), and the mixture was stirred under $H_2$ at 45 psi for 24 h. After filtration through Celite and washing the solids with degassed EtOH (2×5 mL), the filtrate was concentrated in vacuo to afford 0.137 g (60%) of 6 as a brown solid: $^1$H NMR δ 1.35-1.75 (m, 10H), 1.8-2.2 (m, 4H), 2.47-2.59 (m, 2H), 2.82-2.91 (m, 2H), 3.02-3.91 (m, 12H), 4.72-5.0 (m, 2H), 5.21-5.36 (m, 2H), 6.58-6.77 (m, 3H), 6.84-7.2 (m, 3H), 7.24-7.8 (m, 3H); HRMS m/z calcd for $C_{42}H_{53}N_6O_{12}S$, 865.3358 (M+H). found, 865.3466.

$N^1$-(4-Hydroxybutyl)-$N^1$,$N^4$,$N^7$-tris(tert-butoxycarbonyl)norspermidine(9)

4-Chloro-1-butanol (16.5 g, 0.150 mol) was introduced to a mixture of 7 (39.4 g, 0.300 mol), KI (2.475 g, 15.0 mmol), and $K_2CO_3$ (10.5 g, 75.0 mmol) in 1-butanol (375 mL). The mixture was stirred at 125° C. for 24 h, slowly cooled to room temperature, filtered and concentrated under vacuum to afford 8 as a viscous oil, which was dissolved in 50% aqueous THF (500 mL). Di-tert-butyl dicarbonate (130.8 g, 0.600 mol) in THF (100 mL) was added with continuous stirring. After 16 h, volatiles were removed, and the residue was dissolved in $H_2O$ (300 mL) and extracted with EtOAc (200 mL, 3×100 mL). The combined organic layers were washed with 0.5 M citric acid (100 mL), $H_2O$ (100 mL) and saturated NaCl (100 mL) and were concentrated under reduced pressure. Column chromatography using 49:49:2 hexanes/EtOAc/$CH_3OH$ provided 31.73 g (42%) of 9 as a viscous colorless oil. $^1$H NMR δ1.44, 1.45, and 1.46 (3 s, 27H), 1.5-1.8 (m, 9H), 3.02-3.34 (m, 10H), 3.67 (t, 2H, J=5.9), 4.78 and 5.27 (2 br s, 1H); $^{13}$C NMR δ25.20, 27.84, 28.57, 28.60, 28.61, 29.82, 37.72, 44.10, 45.01, 47.01, 62.57, 79.57, 155.75, 156.16, 174.84; HRMS m/z calcd for $C_{25}H_{50}N_3O_7$, 504.3648 (M+H). found, 504.3640. Anal. ($C_{25}H_{49}N_3O_7$) C, H, N.

$N^1$-[4-(Tosyloxy)butyl]-$N^1$,$N^4$,$N^7$-tris(tert-butoxycarbonyl)norspermidine (10)

$N^1$-[4-(Tosyloxy)butyl]-$N^1$,$N^4$,$N^7$-tris(tert-butoxycarbonyl)norspermidine was prepared; calcd for $C_{32}H_{56}N_3O_9S$, 657.3659 (M+H). found, 657.3672. Anal. ($C_{32}H_{55}N_3O_9S$) C, H, N.

$N^1$-[4-(Phthalimido)butyl]-$N^1$,$N^4$,$N^7$-tris(tert-butoxycarbonyl)norspermidine (11)

Potassium phthalimide (1.138 g, 6.15 mmol) was added to 10 (2.70 g, 4.10 mmol) in DMF (50 mL), and the reaction mixture was heated at 90° C. for 48 h. Solvent was removed in vacuo, and the residue was treated with $H_2O$ (50 mL) and extracted with $CHCl_3$ (3×50 mL). The combined organic phase was washed with saturated NaCl and concentrated under reduced pressure. Column chromatography with 4:1 $CHCl_3$/EtOAc generated 1.84 g (71%) of 11. $^1$H NMR δ1.43-1.45 (3 s, 27H), 1.52-1.76 (m, 8H), 3.06-3.29 (m, 10H), 3.71 (t, 3H, J=6.8), 7.70-7.73 (m, 2H), 7.83-7.87 (m, 2H); $^{13}$C NMR δ25.98, 27.46, 28.48, 29.49, 37.40, 37.60, 43.71, 44.87, 46.52, 78.88, 79.43, 79.65, 123.25, 123.41, 132.10, 133.99, 134.11, 155.45, 156.03, 168.41. HRMS m/z calcd for $C_{33}H_{53}N_4O_8$, 633.3858 (M+H). found, 633.3920. Anal. ($C_{33}H_{52}N_4O_8$) C, H, N.

$N^1$-[4-(Phthalimido)butyl]norspermidine Tris(trifluoroacetate) (12)

TFA (25 mL) was added to 11 (3.46 g, 5.47 mmol) in $CH_2Cl_2$ (25 mL) with ice bath cooling, and the solution was stirred for 1 h at 0° C. and 1 h at room temperature. After removal of volatiles in vacuo, the residue was treated with toluene and dried by high vacuum to give 3.69 g (quantitative) of 12 as a white solid: $^1$H NMR ($D_2O$) δ1.72-1.75 (m, 4H), 2.05-2.15 (m, 4H), 3.08-3.19 (m, 10H), 3.71 (t, 3H, J=6.4), 7.81-7.87 (m, 4H); $^{13}$C NMR δ($D_2O$) 23.24, 23.56, 24.37, 25.47, 37.10, 37.53, 44.90, 45.20, 45.29, 47.79, 123.91, 131.71, 135.37, 171.17; HRMS m/z calcd for $C_{18}H_{29}N_4O_2$ 333.2285, (M+H, free amine). found, 333.2324. Anal. ($C_{24}H_{31}F_9N_4O_2$·1.5 $H_2O$) C, H, N.

$N^1$-(2,3-Dimethoxybenzoyl)-$N^7$-[4-(phthalimido)butyl]norspermidine (13)

CDI (0.563 g, 3.48 mmol) was added to a solution of 2,3-dimethoxybenzoic acid (0.633 g, 3.48 mmol) in $CH_2Cl_2$ (5 mL). After stirring for 1 h, the solution was cooled to 0° C. and was added to a suspension of 12 (2.82 g, 4.18 mmol) and $NEt_3$ (2.46 g, 24.4 mmol) in $CH_2Cl_2$ (30 mL). The reaction mixture was stirred for 15 h at room temperature, diluted with $CH_2Cl_2$ (100 mL), and washed with 8% $NaHCO_3$ (50 mL). The organic phase was concentrated in vacuo, and the residue was subjected to flash chromatography eluting with 5% concentrated $NH_4OH$/MeOH to afford 1.20 g (70%) of 13 as a colorless oil: $^1$H NMR δ 1.48-1.57 (m, 2H), 1.62-1.85 (m, 6H), 2.61-2.73 (m, 8H), 3.53 (q, 2H, J=6.0), 3.70 (t, 2H, J=7.6), 3.88 (s, 3H), 3.89 (s, 3H), 7.03 (dd, 1H, J=8.0, 1.6), 7.14 (t, 1H, J=8.0), 7.64 (dd, 1H, J=8.0, 1.6), 7.69-7.71 (m, 2H), 7.82-7.84 (m, 2H), 8.15 (br, 1H, J=7.2); HRMS m/z calcd for $C_{27}H_{37}N_4O_5$, 497.2765 (M+H). found, 497.2671. Anal. ($C_{27}H_{36}N_4O_5$) C, H, N.

$N^4$,$N^7$-Bis[(N-tert-butoxycarbonyl-L-threonyl]-$N^1$-(2,3-dimethoxybenzoyl)-$N^7$-[4-(phthalimido)butyl]norspermidine (14)

A solution of freshly prepared N-tert-butoxycarbonyl-L-threonine N-hydroxysuccinimide ester (4.17 g, 13.2 mmol) in DMF (20 mL) was added to a solution of 13 (2.2 g, 4.4 mmol) in DMF (20 mL). After stirring for 72 h, the solvent was removed under vacuum and the residue was taken up in $CHCl_3$ (50 mL). The organic layer was washed with 5% $NaHCO_3$ (3×50 mL), $H_2O$ (50 mL), and saturated NaCl (50 mL) and was concentrated in vacuo. Flash chromatography eluting with 10% EtOH/EtOAc furnished 2.17 g (55%) of 14 as a white foam: $^1$H NMR δ 1.14-1.22 (m, 6H), 1.38-1.46 (m, 18H), 1.54-2.02 (m, 8H), 2.90-3.61 (m, 10H), 3.68-3.76 (m, 2H), 3.89 (s, 3H), 3.91 (s, 3H), 3.98-4.14 (m, 2H), 5.44-5.68 (m, 2H), 7.04 (d, 1H, J=8.4), 7.14 (d, 1H, J=8.0), 7.62-7.67 (m, 1H), 7.70-7.72 (m, 2H), 7.84-7.86 (m, 2H); HRMS m/z calcd for $C_{45}H_{67}N_6O_{13}$, 899.4767 (M+H). found, 899.4783. Anal. ($C_{45}H_{66}N_6O_{13}$) C, H, N.

$N^4$,$N^8$-Bis[(N-tert-butoxycarbonyl-L-threonyl]-$N^1$-(2,3-dimethoxybenzoyl)-thermospermine (15)

Hydrazine hydrate (5 mL) was added to a solution of 14 (0.350 g, 0.389 mmol) in EtOH (10 mL), and the reaction mixture was stirred at room temperature for 16 h. Solid was filtered, and the filtrate was concentrated in vacuo. The residue was taken up in 1N NaOH (10 mL) and extracted with $CHCl_3$ (3×10 mL), and organic extracts were concentrated. Flash chromatography eluting with 1% concentrated $NH_4OH/MeOH$ gave 195 mg (65%) of 15 as a viscous solid: $^1H$ NMR δ 1.14-1.22 (m, 6H), 1.38-1.46 (m, 18H), 1.54-2.02 (m, 8H), 2.68-2.76 (m, 2H), 2.90-3.61 (m, 10H), 3.89 (s, 3H), 3.91-3.94 (m, 3H), 3.98-4.14 (m, 2H), 4.44-4.62 (m, 2H), 5.46-5.64 (m, 2H), 7.04 (d, 1H, J=8.4), 7.14 (t, 1H, J=8.0), 7.62-7.67 (m, 1H); HRMS m/z calcd for $C_{37}H_{65}N_6O_{11}$, 769.4713 (M+H). found, 769.4709. Anal ($C_{37}H_{64}N_6O_{11}$) C, H, N.

1,36-Bis(2,3-dimethoxybenzoyl)-15,22-dioxo-18,19-dithia-1,5,9,14,23,28,32,36-octaaza-5,9,28,32-tetrakis[(N-tert-butoxycarbonyl-L-threonyl]hexatriacontane (16)

CDI (0.10 g, 0.65 mmol) was added to a solution of 3,3'-dithiopropionic acid (0.06 g, 0.32 mmol) in $CH_2Cl_2$ (2 mL). After stirring for 2 h, a solution of 15 (0.60 g, 0.78 mmol) in $CH_2Cl_2$ (5 mL) was added to the reaction mixture. The solution was stirred for 15 h at room temperature and was diluted with $CH_2Cl_2$ (25 mL). The organic layer was washed with 1N NaOH (15 mL) and saturated NaCl (15 mL) and was concentrated in vacuo. Flash chromatography using 15% EtOH/$CHCl_3$ generated 218 mg (40%) of 16 as a pale-brown solid: $^1H$ NMR δ 1.10-1.25 (m, 12H), 1.29-1.50 (m, 36H), 1.52-2.05 (m, 16H), 2.50-2.65 (m, 4H), 2.90-3.08 (m, 4H), 3.09-3.60 (m, 24H), 3.85-3.98 (m, 12H), 3.99-4.60 (m, 8H), 5.40-5.65 (m, 4H), 6.98-7.15 (m, 2H), 7.18-7.20 (m, 2H), 7.60-7.69 (m, 2H); HRMS m/z calcd for $C_{80}H_{135}N_{12}O_{24}S_2$, 1711.9155 (M+H). found, 1711.9170.

1-(2,3-Dihydroxybenzoyl)-5,9-bis[(N-tert-butoxycarbonyl-L-threonyl]-14-(3-mercaptopropanoyl)-1,5,9,14-tetraazatetradecane Dihydrobromide (17)

Boron tribromide in $CH_2Cl_2$ (1 M, 7.56 mL, 7.56 mmol) was added to a mixture of 16 (340 mg, 0.199 mmol) in $CH_2Cl_2$ (20 mL) at −78° C., and after stirring for 1 h, the reaction mixture was warmed to room temperature and was stirred for 15 h. The reaction mixture was quenched cautiously at 0° C. with $H_2O$ (10 mL) and was stirred for 2 h. The aqueous layer was extracted with $CH_2Cl_2$ (20 mL) and was concentrated in vacuo, and the residue was subjected to a SEPHADEX LH-20 (beaded, cross-linked, hydroxypropylated dextran) column eluting with 40% EtOH/toluene to give 115 mg (73%) of 17 as a white solid: $^1H$ NMR δ 1.15-1.25 (m, 6H), 1.46-2.01 (m, 8H), 2.56-2.63 (m, 2H), 2.94-3.00 (m, 2H), 3.03-3.68 (m, 12H), 4.04-4.20 (m, 2H), 4.24-4.39 (m, 2H), 6.83 (t, 1H, J=8.4), 7.15 (d, 1H, J=8.0), 7.30 (d, 1H, J=7.6); HRMS m/z calcd for $C_{28}H_{49}N_6O_8S$, 629.3333 (M+H, free amine). found, 629.3329. Anal. ($C_{28}H_{50}Br_2N_6O_8S\cdot H_2O$) C, H, N.

4-Methoxybenzyl 2,3-Bis(4-methoxybenzyloxy)benzoate (19)

Sodium hydride (60%, 4.69 g, 0.117 mol) was added in portions to 18 (5.47 g, 35.5 mmol) in DMF (150 mL) with ice bath cooling, and the mixture was stirred at 0° C. for 45 min and at room temperature for 1 h. A solution of 4-methoxybenzyl bromide (25.0 g, 0.124 mol) in DMF (50 mL) was added to the reaction mixture over 30 min. After stirring for 20 h, quenching with $H_2O$ (30 mL) at 0° C. was performed, and solvents were removed under high vacuum. The concentrate was dissolved in EtOAc (200 mL), which was washed with $H_2O$ (100 mL) and saturated NaCl (100 mL); solvent was removed in vacuo. Flash chromatography, eluting with 5:1 hexanes/EtOAc, gave 11.33 g (62%) of 19 as a white solid, mp 108° C.: $^1H$ NMR δ 3.77 (s, 3H), 3.79 (s, 3H), 3.81 (s, 3H), 4.95 (s, 2H), 5.03 (s, 2H), 5.25 (s, 2H), 6.76 (d, 2H, J=8.8), 6.86 (d, 2H, J=8.8), 6.89 (d, 2H, J=8.4), 7.04 (t, 2H, J=7.8), 7.11 (dd, 2H, J=8.0, 2.0), 7.18 (d, 2H, J=8.8), 7.33-7.36 (m, 4H); $^{13}C$ NMR δ 55.32, 55.37, 55.40, 66.81, 71.20, 75.31, 112.97, 113.61, 114.02, 118.16, 123.93, 127.08, 128.19, 128.75, 129.51, 129.73, 130.31, 130.41, 148.43, 152.95, 159.43, 159.62, 159.70, 166.44; HRMS m/z calcd for $C_{31}H_{30}NaO_7$, 537.1889 (M+Na). found, 537.1884.

2,3-Bis(4-methoxybenzyloxy)benzoic Acid (20)

A solution of 19 (8.60 g, 16.71 mmol) in dioxane (84 mL) and 2N NaOH (42 mL) was stirred for 24 h at room temperature. The reaction mixture was concentrated in vacuo. The residue was stirred with $H_2O$ (100 mL) and then acidified to pH 2 with 1N HCl. The white solid was filtered, washed with hexane, and was recrystallised from EtOAc/hexanes to generate 5.93 g (90%) of 20 as a white crystalline solid, mp 129° C.: $^1H$ NMR δ 3.8 (s, 3H), 3.85 (s, 3H), 5.12 (s, 2H), 5.20 (s, 2H), 6.83 (d, 2H, J=8.8), 6.96 (d, 2H, J=9.2), 7.18 (t, 2H, J=8.0), 7.22-7.27 (m, 2H), 7.41 (d, 2H, J=8.4), 7.73 (dd, 1H, J=1.2, 8.0); $^{13}C$ NMR δ 55.36, 55.37, 55.44, 55.46, 71.42, 114.26, 119.12, 123.04, 124.37, 125.00, 126.87, 128.02, 129.73, 131.21, 147.17, 151.45, 159.94, 160.44, 165.45; HRMS m/z calcd for $C_{23}H_{22}NaO_6$, 417.1332 (M+Na). found, 417.1332.

$N^1$-[2,3-Bis(4-methoxybenzyloxy)benzoyl]-$N^7$-[4-(phthalimido)-butyl]norspermidine (21)

CDI (0.239 g, 1.48 mmol) was added to a solution of 20 (0.583 g, 1.48 mmol) in $CH_2Cl_2$ (2 mL). After stirring for 1 h, the solution was cooled to 0° C. and added to a suspension of 12 (1.0 g, 1.48 mmol) and $NEt_3$ (1.05 g, 10.4 mmol) in $CH_2Cl_2$ (2 mL) at 0° C. The solution was stirred for 15 h at room temperature and was diluted with $CH_2Cl_2$ (50 mL). The reaction mixture was washed with 8% $NaHCO_3$ (25 mL) and was concentrated. Flash chromatography eluting with 5% concentrated $NH_4OH/MeOH$ afforded 597 mg (57%) of 21 as a colorless oil: $_1H$ NMR δ 1.48-1.72 (m, 8H), 2.52-2.63 (m, 8H), 3.36 (q, 2H, J=6.0), 3.69 (t, 2H, J=7.2), 3.80 (s, 3H), 3.84 (s, 3H), 4.98 (s, 2H), 5.07 (s, 2H), 6.83 (d, 2H, J=8.8), 6.93 (d, 2H, J=8.4), 7.13 (d, 2H, J=4.8), 7.23 (m, 3H), 7.4 (d, 2H, J=8.4), 7.68-7.7 (m, 2H), 7.81-7.83 (m, 2H), 8.12 (t, 1H, J=7.2); HRMS m/z calcd for $C_{41}H_{49}N_4O_7$, 709.3596 (M+H). found, 709.3611. Anal. ($C_{41}H_{48}N_4O_7$) C, H, N.

$N^4,N^7$-Bis[(N-tert-butoxycarbonyl-L-threonyl]-$N^1$-[2,3-bis(4-methoxybenzyloxy)benzoyl]-$N^7$-[4-(phthalimido)butyl]norspermidine (22)

A solution of freshly prepared N-tert-butoxycarbonyl-L-threonine N-hydroxysuccinimide ester (1.12 g, 3.54 mmol) in DMF (10 mL) was added to a solution of 21 (1.0 g, 1.41 mmol) in DMF (10 mL). After stirring for 72 h at 40° C., the solvent was removed under vacuum, and the residue was taken up in $CHCl_3$ (50 mL). The organic layer was washed with aqueous 5% $NaHCO_3$ (3×50 mL), $H_2O$ (50 mL), saturated NaCl (50 mL) and was concentrated in vacuo. Flash chromatography eluting with 10% EtOH/EtOAc afforded 0.945 g (60%) of 22 as a white foam: $^1H$ NMR δ 1.14-1.21 (m, 6H), 1.37-1.49 (m, 18H), 1.52-1.8 (m, 8H), 3.10-3.60 (m, 10H), 3.68-3.74 (m, 2H), 3.79-3.81 (m, 3H), 3.84 (s, 3H), 3.97-4.11 (m, 2H), 4.32-4.60 (m, 2H), 502 (s, 2H), 5.07 (s, 2H), 5.44-5.62 (m, 2H) 6.82-6.86 (m, 2H), 6.93 (d, 2H, J=8.4), 7.11-7.13 (m, 2H), 7.22-7.26 (m, 3H), 7.39 (d, 2H, J=8.4), 7.69-7.72 (m, 2H), 7.81-7.85 (m, 2H), 8.02 (br s, 1H); HRMS m/z calcd for $C_{59}H_{79}N_6O_{15}$, 1111.5598 (M+H). found, 1111.5650. Anal. ($C_{59}H_{78}N_6O_{15}$) C, H, N.

$N^4,N^8$-Bis[(N-tert-butoxycarbonyl-L-threonyl]-$N^1$-[2,3-bis(4-methoxybenzyloxy)-benzoyl]thermospermine (23)

Hydrazine hydrate (5 mL) was added to a solution of 22 (250 mg, 0.225 mmol) in EtOH (10 mL), and reaction mixture was stirred at room temperature for 16 h. Solid was filtered, and the filtrate was concentrated under high vacuum. The residue was taken up in 1N NaOH (10 mL) and extracted with $CHCl_3$ (3×10 mL), and organic extracts were concentrated. Flash chromatography eluting with 1% concentrated $NH_4OH$/MeOH afforded 198 mg (90%) of 23 as a white solid: $^1H$ NMR δ 1.11-1.22 (m, 6H), 1.37-1.43 (m, 18H), 1.58-2.02 (m, 8H), 2.71 (q, 2H, J=6.0), 2.90-3.60 (m, 10H), 3.80-8.81 (m, 3H), 3.84 (s, 3H), 3.98-4.14 (m, 2H), 4.30-4.60 (m, 2H), 5.00-5.08 (m, 4H), 5.42-5.65 (m, 2H), 6.82-6.86 (m, 2H), 6.93 (d, 2H, J=8.4), 7.13-7.19 (m, 2H), 7.22-7.26 (m, 3H), 7.4 (d, 2H, J=8.4); HRMS m/z calcd for $C_{51}H_{77}N_6O_{13}$, 981.5543 (M+H). found, 981.5589. Anal. ($C_{51}H_{76}N_6O_{13}$) C, H, N.

1,36-Bis[2,3-bis(4-methoxybenzyloxy)benzoyl]-15,22-dioxo-18,19-dithia-1,5,9,14,23,28,32,36-octaaza-5,9,28,32-tetrakis[(N-tert-butoxycarbonyl-L-threonyl]hexatriacontane (24)

CDI (0.063 g, 0.372 mmol) was added to a solution of 3,3'-dithiopropionic acid (0.039 g, 0.186 mmol) in $CH_2Cl_2$ (2 mL). After stirring for 2 h, the solution of 23 (0.550 g, 0.56 mmol) in $CH_2Cl_2$ (5 mL) was added followed by $NEt_3$ (0.025 g, 0.25 mmol). The solution was stirred for 15 h at room temperature and was diluted with $CH_2Cl_2$ (25 mL) was added. The organic layer was washed with 8% $NaHCO_3$ (20 mL) and saturated NaCl (20 mL) and concentrated in vacuo. Flash chromatography using 8% $CH_3OH/CHCl_3$ generated 238 mg (60%) of 24 as a pale-brown solid: $^1H$ NMR δ 1.10-1.23 (m, 12H), 1.25-1.47 (m, 36H), 1.48-2.00 (m, 16H), 2.52-2.70 (m, 4H), 2.80-3.01 (m, 4H), 307-3.55 (m, 24H), 3.80-3.81 (m, 6H), 3.83 (s, 6H), 3.95-4.17 (m, 4H), 4.27-4.62 (m, 4H), 5.01-5.04 (m, 4H), 5.07 (2 s, 4H), 5.42-5.65 (m, 4H), 6.82-6.86 (m, 4H), 6.93 (2 d, 4H, J=8.4), 7.12-7.18 (m, 4H), 7.22-7.27 (m, 6H), 7.4 (d, 4H, J=8.4); HRMS m/z calcd for $C_{108}H_{159}N_{12}O_{28}S_2$ 2137.0859 (M+H). found 2137.0867. Anal. ($C_{108}H_{158}N_{12}O_{28}S_2$) C, H, N.

1,36-Bis(2,3-dihydroxybenzoyl)-15,22-dioxo-18,19-dithia-1,5,9,14,23,28,32,36-octaaza-5,9,28,32-tetrakis(L-threonyl)hexatriacontane Tetrakis(trifluoroacetate) (25)

TFA (25 mL) was added to a mixture of 24 (1.16 g, 0.547 mmol) and anisole (5 mL) in $CH_2Cl_2$ (25 mL) with ice bath cooling, and the solution was stirred for 1 h at 0° C. and 1 h at room temperature. After removal of volatiles in vacuo, the concentrate was subjected to a SEPHADEX LH-20 (beaded, cross-linked, hydroxypropylated dextran) column, eluting with 40% EtOH/toluene to give 0.54 g of 25 (60%) as a white solid: $^1H$ NMR δ 1.24-1.30 (m, 12H), 1.34-1.60 (m, 8H), 1.74-2.21 (m, 8H), 2.57-2.66 (m, 4H), 2.84-2.93 (m, 4H), 3.0-3.64 (m, 24H), 4.04-4.20 (m, 4H), 4.24-4.38 (m, 4H), 6.80-6.86 (m, 2H), 7.03-7.07 (m, 2H), 7.18-7.21 (m, 2H); HRMS m/z calcd for $C_{56}H_{95}N_{12}O_{16}S_2$, 1255.6425 (M+H, free amine). found, 1255.6417. Anal. ($C_{64}H_{98}F_{12}N_{12}O_{24}S_2$·2.5 $H_2O$) C, H, N.

Ethyl 2,3-dihydroxybenzimidate[30] (0.231 g, 1.27 mmol) was added to a solution of 25 (0.35 g, 0.21 mmol) in anhydrous EtOH (15 mL). The mixture was heated at reflux under $N_2$ for 36 h and was concentrated in vacuo. Column chromatography on SEPHADEX LH-20 (beaded, cross-linked, hydroxypropylated dextran), eluting with 15% EtOH/toluene afforded 0.072 g (20%) of 26 as a gray solid: $^1H$ NMR δ 1.35-1.75 (m, 20H), 1.8-2.2 (m, 8H), 2.47-2.59 (m, 4H), 2.82-2.91 (m, 4H), 3.02-3.91 (m, 24H), 4.72-5.0 (m, 4H), 5.21-5.36 (m, 4H), 6.58-6.77 (m, 6H), 6.84-7.2 (m, 6H), 7.8-7.24 (m, 6H); HRMS m/z calcd for $C_{84}H_{103}N_{12}O_{24}S_2$, 1728.6669 (M+H). found, 1728.7344. Anal. ($C_{84}H_{102}N_{12}O_{24}S_2$) C, H, N.

BSA-Cysteine Conjugate (30).

Maleimide-activated protein 28 (2 mg in 100 μL buffer) and cysteine (2 mg in 200 μL of degassed water) were incubated for 8 h at room temperature. After incubation, 30 was purified on a dextran desalting column, eluting with a purification buffer. Fractions (0.5 mL) were collected and the OD was measured at 280 nm. Positive fractions were pooled and protein concentration was estimated by Coomassie assay.

Iron Complex of OVA-VIB Protein Conjugate (31).

A 1-mL solution of 4 (1.685 mg/mL) was incubated at pH 7.4 with 500 μL of FeNTA (1 mM) at room temperature. After incubating 2 h, excess desferrioxamine (1) was added and the mixture again incubated for 2 h. The incubated mixture was subjected to a G-25 Sepharose column, using 30% DMSO/phosphate buffer as an eluting solvent. Fractions (0.5 mL) were collected and the first colored band (fractions 3-6) was eluted; the OD was checked at 280 nm. Protein-containing fractions were pooled (4 mL) and subjected to ICP-MS for estimation of iron content.

Iron Complex of Vibriobactin (33).

Compound 3 (10 mg, 0.0142 mmol) in EtOAc (3 mL) was added to Fe(acac)$_3$ (14.7 mg, 0.0255 mmol) in EtOAc (3 mL). The mixture was shaken with 5 mL of 0.1 M Tris HCl buffer, pH 7.4. The aqueous layer became a deep wine/purple color in 5-10 min. The layers were separated and the aqueous layer was washed with EtOAc (3×5 mL). The aqueous layer was concentrated on high vacuum and subjected to C-18 reversed phase column eluting with 40% aqueous EtOH. Purple-colored fractions were combined and lyophilized to give 8.5 mg of 33 as a purple-colored solid.

Iron Complex of Vibriobactin Disulfide (34).

Compound 26 (50 mg, 0.029 mmol) was dissolved in EtOAc (2 mL) and added to a solution of Fe(acac)$_3$ (28.4 mg, 0.052 mmol) in EtOAc (2 mL). The mixture was shaken well with 5 mL of Tris HCl buffer (0.1 M, pH 7.4). After 10 min, the suspension was collected at the junction of the aqueous layer and the EtOAc layer. The layers were separated and the suspension was washed with Et OAc (5 mL). A small C-18 column was pre-washed with Tris buffer and 50% aqueous EtOH. The iron complex was purified, eluting with 40% aqueous EtOH, then 30% aqueous EtOH. The purple-colored fractions (2 mL each) were collected. The fractions were pooled together and lyophilized to give 36 mg of 34 as a dark purple-colored solid.

Elemental analytical data for synthesized compounds is available via the Internet at pubs.acs.org.

TABLE 1

ELISA Determination of Reactivity of Polyclonal Antibodies
(Serum Titer) Against BSA-VIB and BSA-cysteine.

| | Optical Density at 405 nm[a] | | | | | | | | |
|---|---|---|---|---|---|---|---|---|---|
| | M1 | | | M2 | | | NMS | | |
| Serum Dilution | BSA-VIB | | BSA-cysteine | BSA-VIB | | BSA-cysteine | BSA-VIB | | BSA-cysteine |
| | 23 d | 56 d | 56 d | 23 d | 56 d | 56 d | 23 d | 56 d | 56 d |
| 1:200 | 3.192 | 3.675 | 3.464 | 3.381 | 3.647 | 3.496 | 0.111 | 0.111 | 0.087 |
| 1:400 | 3.295 | 3.749 | 3.340 | 3.370 | 3.692 | 3.496 | 0.106 | 0.095 | 0.077 |
| 1:800 | 2.986 | 3.708 | 2.787 | 3.148 | 3.664 | 3.359 | 0.113 | 0.107 | 0.074 |
| 1:1,600 | 2.230 | 3.586 | 1.676 | 2.867 | 3.637 | 2.975 | 0.087 | 0.087 | 0.072 |
| 1:3,200 | 1.370 | 3.535 | 0.883 | 2.188 | 3.486 | 2.025 | 0.109 | 0.096 | 0.076 |
| 1:6,400 | 0.905 | 2.919 | 0.447 | 1.255 | 2.724 | 1.270 | 0.179 | 0.100 | 0.072 |
| 1:12,800 | 0.476 | 1.756 | 0.254 | 0.809 | 1.718 | 0.736 | 0.106 | 0.095 | 0.080 |
| 1:25,600 | 0.296 | 0.830 | 0.167 | 0.431 | 1.012 | 0.379 | 0.100 | 0.091 | 0.094 |

[a]The optical density of the p-nitrophenol product was determined 1 h after the addition of the p-nitrophenyl phosphate substrate. M1 was immunized with the OVA-VIB conjugate twice s.c. at a dose of 50 µg/immunization; M2 was immunized with the conjugate twice s.c. at 100 µg/immunization. Sera were obtained 23 d and 56 d after the second immunization. Normal mouse sera (NMS) served as a negative control.

TABLE 2

Competitive Binding ELISA of Serum from
Immunized Mice and Non-immunized Mice.

| OVA-VIB Antigen Conc. (µg/mL) | BSA-VIB Antigen: Optical Density at 405 nm[a] | | |
|---|---|---|---|
| | M1 | M2 | NMS |
| 0 | 1.147 | 1.800 | 0.113 |
| 0.08 | 0.486 | 0.926 | 0.109 |
| 0.4 | 0.250 | 0.581 | 0.108 |
| 2 | 0.135 | 0.243 | 0.105 |
| 10 | 0.114 | 0.137 | 0.108 |
| 50 | 0.106 | 0.113 | 0.108 |
| 250 | 0.108 | 0.109 | 0.111 |
| Medium | 0.048 | 0.044 | 0.045 |
| OVA | 1.152 | 1.655 | 0.113 |

[a]The optical density of the p-nitrophenol product was determined 1 h after the addition of the p-nitrophenyl phosphate substrate. Sera from immunized mice (M1 and M2) and normal mice (NMS), diluted 1:10,000, were incubated with the OVA-VIB antigen for 2 h at room temperature. A portion of this mixture was then transferred to an ELISA plate that had been coated with the BSA-VIB antigen, 10 µg/mL. Medium was used as a negative control; unconjugated OVA (10 µg/mL) served as a positive control.

TABLE 3

Reactivity of Antibody-containing Hybridoma Supernatants Against
BSA-VIB and Other Antigens as Measured by an ELISA.

| | Optical Density at 405 nm[a] | | | Optical Density at 405 nm[a] | |
|---|---|---|---|---|---|
| Hybridoma | BSA-VIB | BSA-VIB-iron | BSA-cysteine | IgG (γ-chain) | IgM (µ-chain) |
| 1H8 | 3.662 | 3.040 | 0.100 | 0.608 | 0.091 |
| 2C11 | 3.564 | 3.427 | 0.246 | 3.652 | 0.432 |
| 2D6 | 2.481 | 2.340 | 0.157 | 0.825 | 3.083 |
| 2F5 | 3.173 | 2.832 | 0.180 | 3.530 | 0.120 |
| 2F10 | 2.830 | 2.903 | 0.161 | 2.331 | 0.085 |
| 3F11 | 3.331 | 3.449 | 0.217 | 3.537 | 0.133 |
| 3H9 | 2.824 | 3.663 | 0.486 | 3.808 | 0.389 |
| 4A5 | 1.979 | 2.022 | 0.196 | 2.491 | 0.084 |
| 4A7 | 3.154 | 2.962 | 0.555 | 3.532 | 0.094 |
| 4G3 | 2.399 | 2.130 | 0.170 | 3.500 | 0.097 |
| 5A6 | 3.359 | 3.488 | 0.390 | 2.889 | 0.090 |
| 5D8 | 4.000 | 4.000 | 0.548 | 4.000 | 0.120 |
| Medium | 0.093 | 0.101 | 0.107 | 0.103 | 0.106 |
| M2 (PC) | 3.350 | 3.443 | 1.002 | 3.438 | 0.386 |

[a]The optical density of the p-nitrophenol product was determined 1 h after the addition of the p-nitrophenyl phosphate substrate. Medium served as a negative control; immune mouse serum (M2) in a 1:1,000 dilution was used as a positive control (PC). Hybridoma culture supernatants were undiluted and were screened for antigenic activity 18 days post fusion. Rabbit anti-mouse IgG (whole molecule), at a dilution of 1:1,000, was used to assess the reactivity of the BSA-containing antigens. The class of antibody (IgG or IgM) was determined by the use of goat anti-mouse IgG (γ-chain specific) or goat anti-mouse IgM (µ-chain specific) at a dilution of 1:4,000.

TABLE 4

Recloning of 5A6 Pooled Multiple Colony Wells: ELISA Screening
of Supernatants from Resulting Single Colony Wells Against
BSA-VIB, BSA-VIB-iron, and BSA-cysteine.

| | BSA-VIB Optical Density at 405 nm[a] | | BSA-VIB-iron Optical Density at 405 nm[a] | BSA-cysteine Optical Density at 405 nm[a] |
|---|---|---|---|---|
| Clone | Primary | Secondary | | |
| 1G2 | 4.000 | 3.472 | 3.492 | 0.721 |
| 1G8 | 4.000 | 3.558 | 3.444 | 0.807 |
| 2D5 | 3.408 | 3.575 | 3.579 | 0.689 |
| 2F4 | 3.382 | 3.522 | 3.586 | 0.831 |
| 2G4 | 3.436 | 3.548 | 3.587 | 1.075 |
| 3B9 | 3.395 | 3.473 | 3.418 | 1.130 |
| 3E9 | 3.395 | 3.420 | 3.386 | 0.604 |
| 3G8 | 3.457 | 3.479 | 3.549 | 0.929 |
| 4B5 | 3.421 | 3.503 | 3.534 | 0.636 |
| 4B7 | 3.419 | 3.503 | 3.563 | 0.862 |
| Medium | 0.235 | 0.125 | 0.127 | 0.099 |
| 5A6 (PC) | 3.359 | 3.488 | 3.488 | 0.667 |

[a]The optical density of the p-nitrophenol product was determined 1 h after the addition of the p-nitrophenyl phosphate substrate. Medium was used as a negative control; supernatant from the pooled multiple colony wells from 5A6 served as a positive control (PC). Hybridoma clone culture supernatants were undiluted and were assessed for activity against BSA-VIB 10 days after recloning (primary). The hybridomas were incubated for an additional 5 days, and the supernatants were screened again (secondary). Activity against BSA-VIB-iron and BSA-cysteine were determined 15 days after recloning.

TABLE 5

Reactivity of 5A6 and 2F10 Clone Supernatant Against
BSA-VIB and Other Antigens as Measured by an ELISA.

| Clone | Optical Density at 405 nm[a] | | | Optical Density at 405 nm[a] | |
|---|---|---|---|---|---|
| | BSA-VIB | BSA-VIB-iron | BSA-cysteine | IgG (γ-chain) | IgM (μ-chain) |
| 5A6-1G8 | 3.613 | 3.565 | 0.663 | 3.610 | 0.220 |
| 5A6-2D5 | 3.576 | 3.443 | 0.792 | 2.825 | 0.460 |
| 5A6 (PC) | 3.359 | 3.488 | 0.667 | 3.659 | 0.250 |
| 2F10-1A9 | 3.410 | 3.335 | 0.413 | 3.522 | 0.413 |
| 2F10-2A3 | 2.675 | 2.656 | 0.300 | 2.825 | 0.460 |
| 2F10 (PC) | 2.347 | 2.185 | 0.362 | 2.729 | 0.301 |
| Medium | 0.172 | 0.155 | 0.166 | 0.192 | 0.315 |

[a]The optical density of the p-nitrophenol product was determined 1 h after the addition of the p-nitrophenyl phosphate substrate. Hybridoma clone culture supernatants were undiluted. Medium served as a negative control; supernatant from the pooled multiple colony wells from 5A6, and supernatant from the 2F10 uncloned parent hybridoma, served as positive controls (PC). Rabbit anti-mouse IgG (whole molecule), at a dilution of 1:1,000, was used to assess the reactivity of the BSA-containing antigens. The class of antibody (IgG or IgM) was determined by the use of goat anti-mouse IgG (γ-chain specific) or goat anti-mouse IgM (μ-chain specific) at a dilution of 1:4,000.

TABLE 6

Competitive Binding ELISA of Purified Monoclonal Antibodies
Derived From Clones of 5A6-2D5 and 2F10-1A9.

| OVA-VIB | BSA-VIB Antigen: Optical Density at 405 nm[a] | |
|---|---|---|
| Antigen Conc. (μg/mL) | 5A6-2D5 (Purified mAb) | 2F10-1A9 (Purified mAb) |
| 0 | 2.132 | 3.572 |
| 0.08 | 0.669 | 0.889 |
| 0.4 | 0.483 | 0.879 |
| 2 | 0.189 | 0.497 |
| 10 | 0.145 | 0.137 |
| 50 | 0.113 | 0.109 |
| 250 | 0.093 | 0.095 |
| Medium | 0.092 | 0.090 |
| OVA | 2.190 | 3.214 |

[a]The optical density of the p-nitrophenol product was determined 1 h after the addition of the p-nitrophenyl phosphate substrate. Purified monoclonal antibodies (mAb) were incubated with the OVA-VIB antigen for 2 h at room temperature. A portion of this mixture was then transferred to an ELISA plate that had been coated with the BSA-VIB antigen, 10 μg/mL. Medium was used as a negative control; unconjugated OVA (10 μg/mL) served as a positive control.

The invention claimed is:

1. A method for inducing an immune response in a human or non-human animal against a strain of *Vibrio*, comprising administering to the animal an immunogenic composition comprising a conjugate, wherein the conjugate comprises a siderophore covalently linked to a pharmaceutically acceptable carrier molecule, wherein:

the siderophore is vibriobactin or vulnibactin;

the pharmaceutically acceptable carrier molecule comprises a protein; and the antigenicity of the conjugate is sufficient to stimulate an immunologic response to said conjugate when said conjugate is circulating in the bloodstream of the animal.

2. The method of claim 1, wherein said immunologic response comprises the production of antibodies to at least one outer membrane siderophore receptor, outer membrane siderophore receptor-siderophore complex, or outer membrane siderophore receptor-ferrisiderophore complex of *Vibrio cholerae*.

3. The method of claim 1, wherein the siderophore is vibriobactin.

4. The method of claim 1, wherein the siderophore is vulnibactin.

5. The method of claim 1, wherein said protein comprises a vibriobactin receptor protein.

6. The method of claim 5, wherein the vibriobactin receptor protein is a vibriobactin receptor protein of *Vibrio cholerae*.

7. The method of claim 1, wherein said protein comprises a vulnibactin receptor protein.

8. The method of claim 1, wherein said protein comprises bovine serum albumin (BSA) or ovalbumin (OVA).

9. The method of claim 1, wherein the immunogenic composition further comprises a pharmaceutically acceptable excipient.

10. The method of claim 1 wherein the *Vibrio* species is *Vibrio cholerae* excipient.

* * * * *

UNITED STATES PATENT AND TRADEMARK OFFICE
CERTIFICATE OF CORRECTION

| | | |
|---|---|---|
| PATENT NO. | : 9,125,950 B2 | Page 1 of 1 |
| APPLICATION NO. | : 14/486504 | |
| DATED | : September 8, 2015 | |
| INVENTOR(S) | : Raymond J. Bergeron, Jr. | |

It is certified that error appears in the above-identified patent and that said Letters Patent is hereby corrected as shown below:

*In the claims*

In claim 10, at column 26, lines 40-41, please change the claim as follows:

"The method of claim 1 wherein the *Vibrio* species is *Vibrio cholerae* excipient."

to

--The method of claim 1 wherein the *Vibrio* species is *Vibrio cholerae*.--

Signed and Sealed this
Twenty-third Day of February, 2016

Michelle K. Lee
*Director of the United States Patent and Trademark Office*